United States Patent
Chausson et al.

(10) Patent No.: US 11,896,607 B2
(45) Date of Patent: *Feb. 13, 2024

(54) ANIONICALLY CHARGED CHITOSAN

(71) Applicant: KiOmed Pharma, Herstal (BE)

(72) Inventors: Mickaël Chausson, Huy (BE); Pierre Douette, Embourg (BE); Sandrine Emilia Gautier, Liege (BE); Philippe Vaesen, Saint Remy (BE); Houtaï Choumane, Embourg (BE); Guillermo Rocasalbas, Liege (BE)

(73) Assignee: KiOmed Pharma, Herstal (BE)

( * ) Notice: Subject to any disclaimer, the term of this patent is extended or adjusted under 35 U.S.C. 154(b) by 0 days.

This patent is subject to a terminal disclaimer.

(21) Appl. No.: 16/767,572

(22) PCT Filed: Nov. 9, 2018

(86) PCT No.: PCT/EP2018/080763
§ 371 (c)(1),
(2) Date: May 27, 2020

(87) PCT Pub. No.: WO2019/105718
PCT Pub. Date: Jun. 6, 2019

(65) Prior Publication Data
US 2020/0390799 A1  Dec. 17, 2020

(30) Foreign Application Priority Data
Nov. 28, 2017 (FR) .................. 1761314

(51) Int. Cl.
*A61K 31/722* (2006.01)
*A61K 9/00* (2006.01)
*A61K 31/728* (2006.01)
*C08B 37/08* (2006.01)

(52) U.S. Cl.
CPC .......... *A61K 31/722* (2013.01); *A61K 9/0019* (2013.01); *A61K 31/728* (2013.01); *C08B 37/003* (2013.01)

(58) Field of Classification Search
CPC ..... C08B 37/003; A61P 19/02; A61K 31/722; A61L 27/20
See application file for complete search history.

(56) References Cited

U.S. PATENT DOCUMENTS

| 4,619,995 A * | 10/1986 | Hayes | A23B 7/16 426/302 |
| 5,679,658 A * | 10/1997 | Elson | A61P 43/00 424/424 |
| 6,809,085 B1 | 10/2004 | Elson et al. | |
| 10,612,001 B2 * | 4/2020 | Hazot | A61L 27/3895 |
| 2017/0197009 A1 | 7/2017 | Chausson et al. | |

FOREIGN PATENT DOCUMENTS

| CN | 1431229 A | 7/2003 | |
| CN | 102688195 A | 9/2012 | |
| CN | 103937014 A | 7/2014 | |
| CN | 107325306 A | 11/2017 | |
| DE | 19725037 A1 * | 12/1998 | ........... C08B 37/003 |
| WO | 03068824 A1 | 8/2003 | |
| WO | WO-2005051326 A2 * | 6/2005 | ............ A61K 31/13 |
| WO | WO-2016016463 A1 * | 2/2016 | ........... A61K 31/722 |
| WO | WO-2016087762 A1 * | 6/2016 | ............. A61K 35/32 |
| WO | 2022106676 A1 | 5/2022 | |

OTHER PUBLICATIONS

WO 2016/016463 Machine translation. (Year: 2016).*
Chen, Q. et al "Carboxymethyl-chitosan protects rabbit chondrocytes . . . " Eur. J. Pharmacol., vol. 541, pp. 1-8 (Year: 2006).*
EPO machine translation of DE 19725037. (Year: 1998).*
Rinaudo, M. "Chitin and chtiosan . . . " Prog. Polym. Sci. vol 31, pp. 603-632. (Year: 2006).*
Hirano, S. "Water-soluble glycol chitin and carboxymethylchitin" Meth. Enz., vol. 161, pp. 408-410. (Year: 1988).*
Hongbin, W. et al. "Carboxymethylated chitin reduces MMP-1 expression . . . " Ann. Rheum. Dis., vol. 63, pp. 369-372. (Year: 2004).*
Tokura, S. et al. "O-carboxymethyl chitin concentration . . . " Biomacromol., vol. 2, pp. 417-421. (Year: 2001).*
Zhu, L. et al. "Postoperative anti-adhesion ability of a novel carboxymethyl chitosan . . . " Mater. Sci. Eng., vol. 61, pp. 387-395. (Year: 2016).*
Machine translation of WO 2016/016463. (Year: 2016).*
Li, L. et al "Biodegradable and injectable in situ cross-linking chitosan-hyaluronic acid . . . " Biomaterials, vol. 35, pp. 3903-3917. (Year: 2014).*
Hellebrekers, B. et al "Use of fibrinolytic agents in the prevention of postoperative adhesion formation" Fertility Sterility, vol. 74, No. 2, pp. 203-212. (Year: 2000).*
Anitha et al., "Synthesis, characterization, cytotoxicity and antibacterial studies of chitosan, O-carboxymethyl and N,O-carboxymethyl chitosan nanoparticles", Carbohydrate Polymers 2009, pp. 672-677, vol. 78.
Di Mario et al., "Chitin and Chitosan from Basidiomycetes", International Journal of Biological Macromolecules, 2008, pp. 8-12, vol. 43.
Poon et al., "Cytocompatible Hydrogels Based on Photocrosslinkable Methacrylated O'Carboxymethylchitosan with Tunable Charge: Synthesis and Characterization", Adv. Funct. Mater., 2007, pp. 2139-2150, vol. 17.
Bergeret-Galley "Comparison of Resorable Soft Tissue Fillers", Aesthetic Surgery Journal, Jan./Feb. 2004, pp. 33-46, vol. 24, No. 1.

(Continued)

*Primary Examiner* — Leigh C Maier
(74) *Attorney, Agent, or Firm* — Thompson Coburn LLP; Steven M. Ritchey

(57) ABSTRACT

The present invention relates to a carboxyalkyl chitosan having a zeta potential, measured at pH 7.5, that is less than or equal to −20 mV, compositions comprising same, a process for manufacturing same, and various applications thereof, in particular in the field of therapy, rheumatology, ophthalmology, esthetic medicine, plastic surgery, internal surgery, dermatology or cosmetics.

24 Claims, No Drawings

(56) References Cited

OTHER PUBLICATIONS

Chen et al., "A Novel pH-Sensitive Hydrogel Composed of N,O-Carboxymethyl Chitosan and Alginate Cross-Linked by Genipin for Protein Drug Delivery", Journal of Controlled Release, 2004, pp. 285-300, vol. 96, No. 2.

Czechowska-Biskup et al., "Synthesis of Chitosan and Carboxymethyl Chitosan Hydrogels by Electron Beam Irradiation", Progress on Chemistry and Application of Chitin and its Derivatives, 2016, pp. 27-45, vol. 21.

Deng et al., "Injectable in situ Cross-Linking Chitosan-Hyaluronic Acid Based Hydrogels for Abdominal Tissue Regeneration", Scientific Reports, 2017, pp. 1-13, vol. 7, No. 2699.

Dergunova, et al., "Characterization of Novel Chemically Modified Fungal Polysaccharides as the Macrophage Stimulators", International Immunopharmacology, 2009, pp. 729-733, vol. 9.

Fonseca-Santos et al., "An Overview of Carboxymethyl Derivatives of Chitosan: Their Use as Biomaterials and Drug Delivery Systems", Materials Science and Engineering C, 2017, pp. 1349-1362, vol. 77.

Huang et al., "Injectable Nano-Hydroxyapatite (n-HA)/Glycol Chitosan (G-CS)/Hyaluronic Acid (HyA) Composite Hydrogel for Bone Tissue Engineering", Royal Society of Chemistry, 2016, pp. 1-22.

Kaderli et al., "A Novel Biocompatible Hyaluronic Acid-Chitosan Hybrid Hydrogel for Osteoarthrosis Therapy", International Journal of Pharmaceutics, 2015, pp. 158-168, vol. 483.

Liu et al., "Thermosensitive Injectable In-Situ Forming Carboxymethyl Chitin Hydrogel for Three-Dimensional Cell Culture", Acta Biomaterialia, 2016, pp. 228-237, vol. 35.

Micheels et al., "Effect of Different Crosslinking Technologies on Hyaluronic Acid Behavior: A Visual and Microscopic Study of Seven Hyaluronic Acid Gels", Journal of Drugs in Dermatology, May 2016, pp. 600-608, vol. 15, No. 5.

Ngo et al., "Antioxidant Effects of Chitin, Chitosan, and Their Derivatives", Advances in Food and Nutrition Research, 2014, pp. 15-31, vol. 73.

Rufato et al., "Hydrogels Based on Chitosan and Chitosan Derivatives for Biomedical Applications", IntechOpen, 2018, pp. 1-40.

Skorik et al., "Evaluation of Various Chitin-Glucan Derivatives from Aspergillus Niger as Transition Metal Adsorbents", Bioresource Technology, 2010, pp. 1769-1775, vol. 101.

So, "Improving Patient Compliance with Biopharmaceuticals by Reducing Injection-Associated Pain", J Mucopolysacch Rare Dis, 2015, pp. 15-18, vol. 1.

Song et al., "Peritoneal Adhesion Prevention with a Biodegradable and Injectable N, O-Carboxymethyl Chitosan- Aldehyde Hyaluronic Acid Hydrogel in a Rat Repeated-Injury Model", Scientific Reports, 2016, pp. 1-13, vol. 6, No. 37600.

Ujang et al., "The Development, Characterization and Application of Water Soluble Chitosan", 2011, IntechOpen, pp. 109-130.

Upadhyaya et al., "The Implications of Recent Advances in Carboxymethyl Chitosan Based Targeted Drug Delivery and Tissue Engineering Applications", Journal of Controlled Release, 2014, pp. 54-87, vol. 186.

Valyova et al., "Evaluation of in vitro Antioxidant Activity and Free Radical Scavenging Potential of Variety of Tagetes *Erecta L.* Flowers Growing in Bulgaria", International Journal of Applied Research in Natural Products, 2012, pp. 19-25, vol. 5, No. 2.

Waller et al., "Preventing Friction Induced Chondrocyte Apoptosis: A Comparison of Human Synovial Fluid and Hylan G-F 20", The Journal of Rheumatology, Jul. 2012, pp. 1473-1480, vol. 39, No. 7.

Yang et al., "Ophthalmic Drug-Loaded N,O-Carboxymethyl Chitosan Hydrogels: Synthesis, In Vitro and In Vivo Evaluation", Acta Pharmacologica Sinica, 2010, pp. 1625-1634, vol. 31, No. 12.

Zamani, "Superabsorbent Polymers from the Cell Wall of Zygomycetes Fungi", Department of Chemical and Biological Engineering, Chalmers University of Technology, 2010, pp. 1-68.

Chen et al, "A novel pH-sensitive hydrogel composed of N,O-carboxymethyl chitosan and alginate cross-linked by genipin for protein drug delivery", J of Controlled Release, 2004, pp. 285-300, vol. 96, No. 2.

Luo et al, "Development of carboxymethyl chitosan hydrogel beads in alcohol-aqueous binary solvent for nutrient delivery applications", Food Hydrocolloids, 2013, pp. 332-339, vol. 31, No. 2.

Mi et al, "In vivo biocompatibility and degradability of a novel injectable-chitosan-based implant", Biomaterials, 2002, pp. 181-191, vol. 23, No. 1.

Chen et al., "English Translation of Study on the Substitution and Moisture-Retention Capacity of Carboxymethyl Chitosan", Chinese Journal of Applied Chemistry, Jan. 2001, vol. 18 No. 1.

Liu et al., "Extraction and Characterization of Chitin from the Beetle Holotrichia parallela Motschulsky", Molecules, 2012, pp. 4604-4611, No. 17.

* cited by examiner

ANIONICALLY CHARGED CHITOSAN

CROSS-REFERENCE TO RELATED APPLICATIONS

This application is a U.S. National Phase application of PCT/EP2018/080763 filed on Nov. 9, 2018, claiming the benefit of French Application No. 1761314, filed on Nov. 28, 2017, both of which are incorporated herein by reference in their entireties.

The present invention relates to a carboxyalkyl chitosan, compositions comprising the same, a manufacturing method for manufacturing the same, and various applications thereof, in particular in the field of therapy, rheumatology, ophthalmology, aesthetic medicine, plastic surgery, internal surgery, dermatology or cosmetics.

STATE OF THE ART

Chitosan derivatives are already known, in particular disclosed in the patent applications of Kiomed Pharma published under the numbers WO 2016/016463 and WO 2016/016464 and the corresponding patents. These patent applications focus on the physical, chemical or physico-chemical properties of chitosan derivatives. There however, remains a need for these compositions to be improved, in particular in the context of a therapeutic treatment in a manner so as to provide patients who may have to use such compositions with an optimised therapeutic benefit, and in particular to increase the benefit/risk ratio.

It is possible to obtain a soluble chitosan by increasing the degree of acetylation (DA) by reacetylation of fungal chitosan. It is in effect possible to obtain formulations that are soluble at physiological pH by reacetylation of fungal chitosan, however the following are noted to occur:

- very rapid degradation in vivo or under similar conditions;
- an immune reaction appears in the subject in whom this chitosan is injected or implanted, for example by means of injection or intra-articular implantation;
- the chitosan is not suitable for the targeted applications, and therefore does not serve to secure a sufficiently satisfactory therapeutic use of chitosan, in particular by means of injection or intra-articular implantation.

There are various publications pertaining to the carboxyalkylation of chitosan, and in particular the carboxymethylation of chitosan, essentially with the purpose of solubilising the chitosan. In theory, a chitosan has a formula without an N-acetyl-glucosamine unit, but in practice, the chitosan is derived from chitin, which, for its part, comprises N-acetyl-glucosamine units, and the chitosan has a certain degree of acetylation (DA), which is the proportion of N-acetyl-glucosamine units in the chitosan. The DA of chitosan is generally low. Above that, especially above 30%, it is generally reacetylated chitosan.

Furthermore, the Chinese patent application CN1431229A pertains to carboxymethylated chitosan derivatives, more specifically in respect of the hydrating capacity thereof, however it is limited to this characteristic feature.

The carboxymethylation of chitin derived from animal sources, in particular of crustacean origin, has also been envisaged in the prior art. However, chitin of crustacean origin is difficult to substitute; in particular it is necessary to freeze it and alkalinise it in order to be able to substitute it (see for example the Chinese patent application CN106474569). The process is difficult to implement and in particular to operationalise at industrial scale. On the other hand, such a substitution process based on chitin of crustacean origin is costly in terms of energy, has low reproducibility, and is liable to degrade the polymer and hydrolyse the acetyl groups of the N-acetyl-glucosamine units to a significant extent, while also being difficult to control.

OBJECTS OF THE INVENTION

The object of the invention is to solve the technical problem of providing an appropriate chitosan derivative that is suitable to be used in humans or animals, in particular in the field of therapy, rheumatology, ophthalmology, aesthetic medicine, plastic surgery, internal surgery, dermatology or cosmetics.

More particularly, the object of the invention is to solve the technical problem of providing an appropriate chitosan derivative that is suitable to be used in humans or animals in the therapeutic field, and is in particular usable as a viscosupplement, and in particular has the ability to be injected into or mixed with synovial fluid.

The object of the invention in particular is to solve the technical problem of providing a reconstructed synovial fluid, that is to say a composition that restores the properties of a joint, for example by providing it with a capacity to lubricate the surfaces of cartilage.

Another object of the invention is to solve the technical problem of providing a chitosan derivative, or a composition comprising the same, that exhibits good properties and compatibility in a mixture with a synovial fluid, and in particular a synovial fluid of a human or an animal subject, for example in order to treat an articular or joint pathology or deterioration of the synovial fluid in question.

The object of the invention is also to solve the technical problem of providing a chitosan derivative, or a composition comprising the same, which limits the immune reaction of a subject, and in particular of a human or an animal subject, who receives such administration, for example by means of injection, of a chitosan derivative or a composition comprising the same.

Another object of the invention is also to solve the technical problem of providing a chitosan derivative, or a composition comprising the same, which presents characteristics that have low variability based on the pH.

The object of the invention is also to solve the technical problem of providing a chitosan derivative, or a composition comprising the same, that has a suitable osmolality and a pH value deemed appropriate for use thereof in contact with the tissue of a human or an animal subject, and acceptable in terms of lifespan in situ, immunological reaction and/or foreign body reaction and biomechanical properties, depending on the targeted therapeutic indication, in particular in the context of regenerative medicine.

DESCRIPTION OF THE INVENTION

It has been discovered in a surprising manner that a chitosan derivative according to the present invention makes it possible to solve at least one, and preferably all, of the technical problems described here above.

It has been discovered in a surprising manner that a chitosan derivative exhibiting an electrostatic charge (characterised by its zeta potential) over a pH range around the pH of the medium in which it is administered, and in particular at pH equal to 7.5, that is lower than a certain value made it possible to solve at least one, and preferably all, of the technical problems described or suggested. In particular, such a chitosan derivative provides the means to limit the immune response of a subject to whom the chitosan derivative or a composition comprising the same has been administered, typically by means of injection or implantation.

The present invention relates, according to a second aspect, to a chitosan derivative having glucosamine units, N-acetyl-glucosamine units and glucosamine units substituted by a carboxyalkyl group, the said carboxyalkyl chitosan having a zeta potential, measured at pH 7.5, that is lower than or equal to −10 mV, and preferably lower than or equal to −15 mV.

In particular, it has been discovered that a chitosan derivative of fungal origin makes it possible to solve at least one, and preferably all, of the technical problems described or suggested. In particular, a chitosan derivative of fungal origin provides the means to limit the immune response of a subject to whom the chitosan derivative or a composition comprising the same has been administered, typically by means of injection or implantation.

The present invention relates, according to a first aspect, to a carboxyalkyl chitosan of fungal origin having glucosamine units, N-acetylglucosamine units and glucosamine units substituted by a carboxyalkyl group, the said carboxyalkyl chitosan preferably having a degree of substitution by a carboxyalkyl group that is greater than 20%, expressed as the number of moles of the substituent in relation to the number of moles of total units.

Reference is also made to a chitosan derivative or substituted chitosan derivative.

The chitosan is for example referenced under Chemical Abstracts Service Registry Number (CAS number) 9012-76-4.

The chitosan used for the invention is advantageously of fungal origin, and preferably is derived from the mycelium of a fungus of the type Ascomycetes, and in particular from *Aspergillus niger*, and/or from a fungus Basidiomycetes, and in particular *Lentinula edodes* (shiitake) and/or *Agaricus bisporus* (button mushroom). Preferably, the chitosan is derived from *Agaricus bisporus*. The chitosan is preferably very pure, that is to say with extremely low impurity content deriving from its fungal origin or from the manufacturing process, and of a microbiological quality that is compatible with its use as an implant or pharmaceutical composition. One preparation method for preparing chitosan is the one described in the patents WO 03/068824 (EP 1483299; U.S. Pat. No. 7,556,946). In general, the chitin is placed in aqueous suspension in the presence of sodium hydroxide, thereafter the medium is brought to a high temperature for a variable duration that varies according to the desired molecular mass. The chitosan is subsequently purified by solubilisation in an acid medium and precipitated in an alkaline medium, then washed and dried.

Preferably, the chitosan is of sufficiently pure grade appropriate for pharmaceutical use.

The chitosan is advantageously purified and then preferably dried. After purification, the method of the invention may include a step of drying the carboxyalkyl chitosan, then optionally grinding it in order to obtain a powder. The carboxyalkyl chitosan may be dried for example by evaporation of the water, for example by means of a spray-drying process, by a fluidised bed process, or by heat drying under vacuum or at atmospheric pressure, or even by lyophilisation.

The carboxyalkyl chitosan may be solubilised in an aqueous solution, and for example in water of pharmaceutically acceptable quality suitable for injection or implantation in a body, and in particular in a human body.

The chitosan prepared may be of various different molecular masses, and generally ranging from 10,000 to 500,000.

According to one variant, the average molecular mass is comprised between 20,000 and 60,000.

According to another variant, the average molecular mass is comprised between 60,000 and 100,000.

According to another variant, the average molecular mass is comprised between 100,000 and 120,000.

According to another variant, the average molecular mass is comprised between 120,000 and 150,000.

According to another variant, the average molecular mass is comprised between 150,000 and 220,000.

According to another variant, the average molecular mass is comprised between 220,000 and 300,000.

According to another variant, the average molecular mass is comprised between 300,000 and 500,000.

When the chitosan is crosslinked, the molecular mass of the crosslinked polymer may indeed be much higher.

It is possible to hydrolyse chitosan in order to reduce its molecular mass.

Preferably here, the average molecular mass is the average molecular mass in viscosity (Mv), calculated based on the intrinsic viscosity according to the Mark-Houwink equation. The intrinsic viscosity is measured by means of capillary viscometry, with a capillary viscometer of the Ubbelohde type, according to the method of monograph 2.2.9 of the European Pharmacopoeia. Measurement of the flow time for the solution to flow through a suitable capillary tube (Lauda, for example the Ubbelohde 510 01 capillary tube with a diameter of 0.53 mm) is done by means of an automatic viscometer I-Visc (Lauda), firstly at the initial chitosan concentration, then for several dilutions, for example according to the recommendations in monograph 2.2.9. The reduced intrinsic viscosity is inferred therefrom for each of the concentrations. The reduced viscosity is plotted as a function of the temperature, and the value at concentration 0 is extrapolated in order to infer therefrom the intrinsic viscosity. For example it is necessary to plot the reduced viscosity ($h_{red}$ in mL/g) of i dilutions as a function of the concentration C of the i dilutions (g/mL) in accordance with the Formula 5.

$$[h_{red}] = (t_1 - t_0) - (t_1 - t_0).\qquad\text{Formula 2.}$$

In order to calculate the average viscosimetric mass, the Mark-Houwink equation is applied with the constants k and alpha recommended by Rinaudo et al. (in: Int J Biol Macromol, 15, 281, 1993), according to the degree of acetylation (DA) of chitosan, in accordance with one of the following three formulae.

$$Mv = ([h]/0.082)^{(1/0.76)}, \text{ for a DA of 2\%;}\qquad\text{Formula 3.}$$

$$Mv = ([h]/0.076)^{(1/0.76)}, \text{ for a DA of 10\% (for example 11.5\%);}\qquad\text{Formula 4.}$$

$$Mv = ([h]/0.074)^{(1/0.76)}, \text{ for a DA of 20\% (for example 21\%).}\qquad\text{Formula 5.}$$

For intermediate DA values, a linear interpolation is carried out in order to calculate the average viscosimetric mass (Mv).

Preferably, the chitosan used has an average molecular mass comprised between 120,000 and 150,000, or even between 150,000 and 220,000, or indeed even between 220,000 and 300,000, or even above 300,000, and in general up to 500,000.

It is also possible measure the final molecular mass of the carboxyalkyl chitosan: it is possible for example to measure its intrinsic viscosity by means of capillary viscosity, infer therefrom its average molecular mass (Mw) (by determining beforehand the parameters K and alpha of the carboxyalkyl chitosan), or by a chromatographic method, for example by gel permeation chromatography.

Typically, in the carboxyalkyl chitosan according to the invention, the glucosamine units are D-glucosamine units (D-glucosamine units, N-acetyl-D-glucosamine units, and with at least one of the D-glucosamine units and the N-acetyl-D-glucosamine units being substituted).

According to one variant, a substituted chitosan has a substitution of only the D-glucosamine units.

According to another variant, a substituted chitosan has a substitution of the D-glucosamine and the N-acetyl-D-glucosamine units simultaneously, in which the carboxyalkyl group is covalently bound, according to one variant to the amine groups of the chitosan only, or according to another variant to the amine and hydroxyl groups of the chitosan simultaneously.

The substitution is generally only partial, not all of the units are necessarily substituted.

According to one embodiment, the degree of substitution of the D-glucosamine units expressed in number of moles of D-glucosamine units in relation to the number of moles of total units (D-glucosamine and N-acetyl-D-glucosamine units, either substituted or not substituted) of the substituted chitosan, ranges from 30% to 250%.

According to one embodiment, the degree of substitution by a carboxyalkyl group is greater than 50%, expressed in number of moles of the substituent in relation to the number of moles of total units.

According to one embodiment, the degree of substitution of the D-glucosamine units expressed in number of moles of D-glucosamine units in relation to the number of moles of total units (D-glucosamine and N-acetyl-D-glucosamine units, either substituted or not substituted) of the substituted chitosan, ranges from 50% to 200%, and more preferably is greater than 70%.

According to one embodiment, the degree of substitution by a carboxyalkyl group is less than 80%, expressed in number of moles of the substituent in relation to the number of moles of total units.

Typically, the substitution is brought out by covalent bonding.

According to one variant, the carboxyalkyl chitosan is an N,O-carboxyalkyl chitosan. The proportion of units substituted by a carboxyalkyl group in the 0-position (either 03 or 06 of the glucosamine and/or N-acetyl-glucosamine units) and/or in the N position (of the glucosamine units) varies. The degree of substitution may therefore be greater than 100%.

Advantageously, the degree of substitution (DS) and the degree of acetylation (DA) of the carboxyalkyl chitosan are measured by means of solid-state carbon-13 nuclear magnetic resonance (NMR) spectroscopy, by using a Bruker Spectrometer (Avance III HD 400 MHz), equipped with a PH MAS VTN 400SB BL4 NP/H probe. For example, the spectrum is recorded at ambient temperature, with a relaxation time ranging from 1 to 8 seconds, and a number of scans ranging from 64 to 512. The areas of the carbon signals are determined after deconvolution. The carbons considered are the following: "acetyl CH3" (methyl carbon of the acetyl group of the N-acetyl-glucosamine units, either substituted or not substituted), "C1" (carbon at position 1 of the glucosamine and N-acetyl-glucosamine units) and "C=O" (carbonyl carbon of the carboxymethyl substituent and carbonyl carbon C=O of the acetyl group of the N-acetyl-glucosamine units, either substituted or not substituted). In order to determine the DS of a given carboxyalkyl chitosan, it is also necessary to record the carbon 13 NMR spectrum of the precursor chitosan of this carboxyalkyl chitosan. Based on the precursor chitosan spectrum, the "CSU ratio" is calculated, that is to say the ratio between the area of the signal of the "acetyl CH3" group (methyl carbon of the acetyl group of the N-acetyl-glucosamine units) and the area of the signal of the "C=0" (carbonyl carbon of the acetyl group of the N-acetyl-D-glucosamine units). The DA of the carboxyalkyl chitosan is calculated in accordance with the Formula 1, and the DS in accordance with the Formula 2, where I represents the area of the signal of the carbon considered.

$$DA = \frac{I_{acetyl\,CH3}}{I_{C_1}} \qquad \text{Formula 1}$$

$$DS = \frac{I_{C=0} - I_{CH3}/CsU \text{ Ratio}}{I_{C_1}} \qquad \text{Formula 2}$$

The DA and the DS may be determined by making use of other known methods for carboxyalkyl chitosans, for example by means of proton NMR in aqueous medium, using a magnetic resonance spectrometer, for example according to the method described by Liu et al. (in: Carb Polym 137, 600, 2016), for example with a prior hydrolysis of carboxyalkyl chitosan by adding therein a concentrated solution of deuterated hydrochloric acid prior to analysis.

If there is another NMR method that is more advantageous for estimating the degree of substitution in a reliable manner, that alternative method should be used. The above methods are to be adapted by a person skilled in the art with regard to the preparation of the sample and the signals to be integrated, in particular as a function of the resolution, the robustness and the position of the protons of the signals to be used for calculating the degree of substitution.

The degree of carboxyalkylation of chitosan may advantageously vary from 20 to 250%, preferably from 50 to 200%, and for example from 70 to 170%, expressed in number of moles of carboxyalkyl in relation to the number of moles of total units.

According to one variant, the degree of carboxyalkylation of chitosan may advantageously vary from 40 to 130%, and for example from 70 to 130%, expressed in number of moles of carboxyalkyl in relation to the number of moles of total units.

The degree of substitution of chitosan is typically correlated with the mass ratio of the starting reagents in relation to the chitosan at the start of the reaction. By way of carboxyalkylating agents, mention may be made of acid chlorides (or the salts thereof, for example sodium monochloroacetate), such as for example those bearing one or more carboxymethyl, carboxyethyl, carboxypropyl, carboxybutyl groups, etc.

According to one variant, the present invention relates to a carboxyalkyl chitosan in which the alkyl portion of the carboxyalkyl is a C1-C5 alkyl group, either linear or branched.

According to one variant, the present invention relates to a carboxymethyl chitosan.

According to this variant, the substituted chitosan is an N-carboxyalkylated chitosan.

According to this variant, the substituted chitosan is an O-carboxyalkylated chitosan.

According to this variant, the substituted chitosan is an N-carboxyalkylated and O-carboxyalkylated chitosan.

Advantageously, the zeta potential, measured at pH 7.5, is less than or equal to −18 mV.

Advantageously, the carboxyalkyl chitosan has a zeta potential, measured at pH 7.5, that is less than or equal to −22 mV, and preferably less than or equal to −24 mV.

According to one specific variant, the substituted chitosan preferably has an average molecular mass of 150,000 to 220,000 and a degree of substitution ranging from 50 to 200%, the molecular mass preferably being expressed prior to substitution.

According to another specific variant, the substituted chitosan has an average molecular mass of 120,000 to 150,000, and a degree of substitution ranging from 70 to 200%, the molecular mass preferably being expressed prior to substitution.

According to one specific variant, the substituted chitosan preferably has an average molecular mass of 220,000 to 300,000 and a degree of substitution ranging from 70 to 200%, the molecular mass preferably being expressed prior to substitution.

According to another specific variant, the substituted chitosan has an average molecular mass of 220,000 to 300,000 and a degree of substitution ranging from 50 to 200%, the molecular mass preferably being expressed prior to substitution.

According to another specific variant, the substituted chitosan has an average molecular mass of 300,000 to 500,000 and a degree of substitution ranging from 50 to 200%, the molecular mass preferably being expressed prior to substitution.

According to another specific variant, the substituted chitosan has an average molecular mass of 300,000 to 500,000 and a degree of substitution ranging from 70 to 200%, the molecular mass preferably being expressed prior to substitution.

According to one specific variant, the substituted chitosan preferably has an average molecular mass of 120,000 to 150,000 and a degree of substitution ranging from 20 to 50%, the molecular mass preferably being expressed prior to substitution.

According to another specific variant, the substituted chitosan has an average molecular mass of 220,000 to 300,000 and a degree of substitution ranging from 20 to 50%, the molecular mass preferably being expressed prior to substitution.

According to another specific variant, the substituted chitosan has an average molecular mass of 300,000 to 500,000 and a degree of substitution ranging from 20 to 50%, the molecular mass preferably being expressed prior to substitution.

According to one specific variant, the substituted chitosan has a degree of substitution ranging from 20 to 80%, and preferably from 40 to 60%, and a degree of acetylation ranging from 20 to 80%, and preferably from 30 to 75%.

According to one specific variant, the substituted chitosan has a degree of substitution ranging from 50 to 200%, and preferably from 70 to 200%, and a degree of acetylation ranging from 20 to 80%, and preferably from 30 to 75%.

According to one specific variant, the substituted chitosan has a degree of substitution ranging from 50 to 200%, and preferably from 70 to 200%, and a degree of acetylation ranging from 20 to 50%, and preferably from 20 to 40%.

According to one specific variant, the substituted chitosan has a degree of substitution ranging from 50 to 200%, and preferably from 70 to 200%, and a degree of acetylation ranging from 50 to 75%.

According to another specific variant, the substituted chitosan has a degree of substitution ranging from 90 to 200%, and preferably from 90 to 150%, and a degree of acetylation ranging from 20 to 80%, the molecular mass preferably being expressed prior to substitution.

According to one specific variant, the substituted chitosan has a degree of substitution ranging from 90 to 200%, and preferably from 90 to 150%, and a degree of acetylation ranging from 20 to 50%, and preferably from 20 to 40%.

According to one specific variant, the substituted chitosan has a degree of substitution ranging from 90 to 200%, and preferably from 90 to 150%, and a degree of acetylation ranging from 50 to 75%.

According to one specific variant, the substituted chitosan preferably has an average molecular mass of 220,000 to 300,000, a degree of substitution ranging from 90 to 200%, and preferably from 90 to 150%, and a degree of acetylation ranging from 50 to 75%, the molecular mass being preferably expressed prior to substitution.

According to one variant, the carboxyalkyl chitosan is crosslinked. Thus, several chitosan chains may be crosslinked, for example by reaction with a crosslinking agent, such as for example crosslinking agents used for the crosslinking of polysaccharides, such as for example genipin, butyl biglycidyl ether, glutaraldehyde, epichlorohydrin, 1-bromo-3,4-epoxybutane, 1-bromo-4,5-epoxypentane, l-chloro-2,3-epithio-propane, 1-bromo-2,3-epithiopropane, 1-bromo-3,4-epithio-butane, 1-bromo-4,5-epithiopentane, 2,3-dibromopropanol, 2,4-dibromobutanol, 2,5-dibromopentanol, 2,3-dibromopropanethiol, 2,4-dibromobutanethiol, and 2,5-dibromopentane-thiol epichlorohydrin, 2,3-dibromopropanol, 1-chloro-2,3-epithiopropane, dimethylaminopropylcarbodiimide, oxidised dextran, gallic acid, epigallocatechin gallate, curcumin, tannic acid, or even diisocyanate compounds such as hexamethylene diisocyanate or toluene diisocyanate.

With a crosslinked carboxyalkyl chitosan the molecular mass may be very high.

By substituting the chitosan, it was possible to prepare a solution of a carboxyalkyl chitosan that is soluble in an aqueous solution whose pH varies over a wide range, while the unsubstituted chitosan is soluble only at a pH below 5.5 to 6.5. The carboxyalkyl chitosan thus has an ability to be solubilised at various different pH values thanks to the presence of carboxyalkyl groups that modify its solubility profile, and in particular at physiological pH or at the pH of physiological fluids that are modified by a pathology, for example an inflammatory pathology. It is known that the pH of physiological fluids such as the synovial fluid of a joint, the aqueous humour, the vitreous humour, and tears, can vary in a significant manner between individuals, due to various factors such as age, pathology, etc. It is therefore advantageous that the carboxyalkyl chitosan is able to remain soluble over a wide pH range, for example from 6.0 to 8.5, or even from 5.0 to 8.5, or indeed even from 4.5 to 8.5.

According to one embodiment, the substituted chitosan formulation has an osmolality of 100 to 700 mosm/kg, preferably of 200 to 500 mosm/kg.

Advantageously, the osmolality of the substituted chitosan formulation is comprised between 250 and 400 mosm/kg, and preferably from 275 to 325 mosm/kg.

According to one variant, the substituted chitosan formulation has an osmolality that is compatible with a joint.

According to one variant, the substituted chitosan formulation has an osmolality that is compatible with an ocular or intraocular surface.

It is preferable that the osmolality of the substituted chitosan formulation be comprised between 250 and 400, and more specifically between 250 and 380 mosm/kg.

The term "soluble in water" is understood to indicate that the carboxyalkyl chitosan does not exhibit any turbidity visible to the naked eye when it is placed in aqueous solution. More specifically, it is possible to confirm the solubility, that is to say the absence of any turbidity, of a solution of carboxyalkyl chitosan at a concentration for example of 1% (m/m) in water or a buffer, for example a phosphate buffer, with/for an optical density of less than 0.5, and preferably less than 0.2, as measured by UV-visible spectrometry at the wavelength of 500 nm with reference to a reference tank comprising only the aqueous solvent used for the sample measured, but in the absence of the substituted chitosan. Another method consists of a visual inspection according to monograph 2.9.20 of the European Pharmacopoeia. When the chitosan is not sufficiently substituted, the composition is not soluble in a satisfactory pH range, for example ranging from pH 6.0 to pH 8.5, at ambient temperature.

The degree of acetylation (DA) of chitosan is determined as for example described in the patent applications WO 2017009335 and WO 2017009346 by means of potentiometric titration. The DA may alternatively be measured by other methods known for chitosan, such as proton nuclear magnetic resonance (NMR) spectroscopy, solid-state carbon-13 NMR, infrared spectrometry.

Advantageously, the carboxyalkyl chitosan has a degree of acetylation comprised between 5 and 80%, expressed in number of moles of N-acetyl-glucosamine units in relation to the number of moles of total units. The degree of acetylation is expressed in number of N-acetyl-D-glucosamine units in relation to the number of total N-acetyl-D-glucosamine and D-glucosamine units present.

Advantageously, the carboxyalkyl chitosan has a degree of acetylation comprised between 40 and 80%, expressed in number of moles of N-acetyl-glucosamine units in relation to the number of moles of total units.

According to one variant, the degree of acetylation ranges from 5 to 20%.

According to one variant, the degree of acetylation ranges from 15 to 25%.

According to one variant, the degree of acetylation ranges from 20 to 45%.

According to one variant, the degree of acetylation ranges from 20 to 30%.

According to one variant, the degree of acetylation ranges from 25 to 40%.

According to one variant, the degree of acetylation ranges from 40 to 50%.

According to one variant, the degree of acetylation ranges from 50 to 60%.

According to one variant, the degree of acetylation ranges from 60 to 75%.

The degree of acetylation is determined by means of 13 carbon NMR or by proton NMR, according to the same method as for the determination of the DS. The carboxyalkyl chitosan advantageously has a controlled degree of acetylation. The term "chitosan having a controlled degree of acetylation" is understood to refer to a product for which the degree of acetylation, that is to say the proportion of N-acetyl-glucosamine units, may be adjusted in a controlled manner, in particular by an acetylation reaction.

According to one variant, a composition according to the invention may be in the form of a solution and is not able to be gelled by variation of the temperature (not capable of thermogelling).

According to one variant, the rheological characteristics of a solution according to the invention may change with the temperature, but without going through a sol-gel transition. The rheological characteristics of a solution according to the invention may in particular be evidenced by the modulus of elasticity (G') and/or the loss modulus (G"), or even the complex modulus G*.

According to one variant, the rheological characteristics of a solution according to the invention are substantially constant no matter what the temperature.

According to one variant, a composition according to the invention may be in the form of a solution and be capable of thermogelling.

According to one variant, a composition according to the invention may be in the form of a gel and not be capable of thermogelling.

The invention therefore makes it possible, according to one variant, to prepare a composition capable of thermogelling that is fluid at a temperature below the temperature of use, typically at a temperature lower than the physiological temperature, for example of 37° C., but which is in the form of a gel at the temperature of use, typically at the physiological temperature, for example of 37° C., at neutral pH (pH 7) or at physiological pH, and for example from 7 to 8.5, with an osmolality that is suitable for the envisaged use. It is for example a physiological osmolality.

According to one variant, the composition capable of thermogelling has a thermoreversible sol-gel transition.

Advantageously, the present invention makes it possible to provide a composition with a low concentration of substituted chitosan.

Advantageously, the concentration of carboxyalkyl chitosan is less than 10%, for example less than or equal to 5%, by mass in relation to the total mass of the composition (m/m).

According to one variant, the concentration of chitosan is less than 4%, for example less than or equal to 3%, or even for example less than or equal to 2% by mass in relation to the total mass of the composition (m/m).

Advantageously, the composition of the invention may also comprise a biopolymer other than the substituted chitosan. According to one advantageous variant, the biopolymer is a polysaccharide, whether or not oxidised, either crosslinked or not crosslinked by covalent bonds, for example hyaluronic acid or sodium hyaluronate.

The hyaluronic acid may have a molecular mass up to 5 million Da. The molecular mass of hyaluronic acid may be reflected by its intrinsic viscosity or by its dynamic viscosity in solution. Hyaluronic acid may have a density ranging from 1 to 4 m$^3$/kg, and for example be characterised as having low (for example approximately 1 to 2 m$^3$/kg) or high (for example approximately 2 to 4 m$^3$/kg) molecular mass.

Advantageously, the concentration of hyaluronic acid is less than 4%, for example less than or equal to 3%, or even for example less than or equal to 2% by mass in relation to the total mass of the composition (m/m).

According to one specific variant, the concentration of hyaluronic acid is less than 1.9% (m/m), expressed in mass in relation to the mass of the final composition. Advantageously, the concentration of hyaluronic acid is comprised between 0.5 and 1.5% (m/m), expressed in mass in relation to the mass of the final composition. According to one particular variant, the concentration of hyaluronic acid is approximately 0.9%, 1.0%, 1.1%, 1.2%, 1.3%, 1.5% (m/m), expressed in mass in relation to the mass of the final composition.

The ratio between chitosan and hyaluronic acid may for example vary from 5 to 95%, for example from 10 to 90%, and even for example from 30 to 70% of substituted chitosan, and from 5 to 95%, for example from 10 to 90%, and even for example from 30 to 70% respectively, of hyaluronic acid, the percentages expressed in respect of: dry mass of substituted chitosan/dry mass of hyaluronic acid. According to one variant, this ratio between chitosan and hyaluronic acid is 1/1 (that is 50% of chitosan and 50% of hyaluronic acid). According to another variant, the ratio between chitosan and hyaluronic acid is 1.5/0.5 (that is 75% of chitosan and 25% of hyaluronic acid).

According to one variant, the hyaluronic acid may be crosslinked between different chains of hyaluronic acid.

The present invention also relates to a preparation method for preparing the carboxyalkyl chitosan.

According to one variant, the preparation method for preparing the carboxyalkyl chitosan according to the invention includes the preparation of a chitosan of fungal origin, the reacetylation of the chitosan, and the carboxyalkylation of the reacetylated chitosan.

Thus, the invention relates to a reacetylated chitosan or a reacetylated carboxyalkyl chitosan.

According to one embodiment, it is thus possible to dissolve chitosan in an aqueous medium, preferably slightly acidified (pH 6 for example). Acetic anhydride may be added to the chitosan solution one or more times. A basic agent is then added, such as, for example, sodium hydroxide and/or urea. Thereafter an alkylating agent such as, for example, sodium monochloroacetate (that is to say the sodium salt of chloroacetic acid) or chloroacetic acid is then added, subsequently the substituted chitosan is purified, recovered and dried.

According to one variant, the preparation method for preparing the carboxyalkyl chitosan according to the invention includes the preparation of a chitosan, the carboxyalkylation of the chitosan, then the reacetylation of the carboxyalkylated chitosan. Advantageously, such a method serves to enable a precise control of the degree of acetylation of the final carboxyalkyl chitosan, and in particular to obtain a high degree of acetylation, for example above 40%. Thus, the invention relates to a reacetylated then carboxyalkylated chitosan or a reacetylated carboxyalkyl chitosan.

According to one variant, the preparation method for preparing the carboxyalkyl chitosan according to the invention includes the preparation of a chitin of fungal origin, the carboxyalkylation of the chitin, and optionally the reacetylation of the carboxyalkylated chitin in order to obtain the carboxyalkyl chitosan according to the invention.

According to one variant, the preparation method for preparing the carboxyalkylated chitosan according to the invention includes the preparation of a chitin of fungal origin, a deacetylation of the chitin, the carboxyalkylation of the chitin, and optionally the reacetylation of the carboxyalkylated chitin in order to obtain the carboxyalkyl chitosan according to the invention.

According to one embodiment, the carboxyalkylation step includes an alkalinisation step for alkalinisation of the hydroxyl groups of the chitosan, in order to promote a high degree of substitution, and for example both in the N-position of the glucosamine units and the O-position of the glucosamine and N-acetyl-glucosamine units.

According to one embodiment, the method of the invention includes an alkalinisation step comprising the dispersion of chitosan in an alcohol solution, such as isopropanol in the presence of a basic agent such as for example sodium hydroxide, and agitation for a period of at least one hour at a temperature of minimum −32° C. and preferably maximum 15° C. To this suspension is then added an alkylating agent such as, for example, monochloroacetic acid. Thereafter the substituted chitosan is purified, recovered, and then dried.

According to one variant, the preparation method for preparing the carboxyalkylated chitosan according to the invention includes the preparation of a chitosan, the carboxyalkylation of the chitosan and subsequently the reacetylation of the carboxyalkylated chitosan.

According to one embodiment, the carboxyalkylation step does not include an alkalisation step.

The step of reacetylation of a carboxyalkyl chitosan may for example include one or more additions of acetic anhydride to the carboxyalkyl chitosan solution.

The final steps of purification, filtration and drying in order to collect the purified carboxyalkyl chitosan are carried out according to known methods with a view to obtaining a carboxyalkyl chitosan according to the desired degree of purity, which in general depends on the application envisaged, such as for example by cycles of precipitation and solubilisation or by dialysis.

According to one variant, the ratio of acetic anhydride/chitosan (volume/mass) varies between 0.1 and 10, and preferably from 0.1 to 2, during the reacetylation step.

According to one variant, the mass ratio of carboxyalkylating agent/chitosan varies between 1 and 50, and preferably from 2.5 to 25, during the carboxyalkylation step.

According to one variant, use is made of a mass ratio of the reagents that provide the carboxyalkyl group (that is to say the alkylating agent) relative to the basic agent that is necessary and sufficient to obtain the desired degree of substitution. For example, the mass ratio of the alkylating agent to the basic agent is greater than 1 and less than 10, and preferably ranges from 1.4 to 3.3.

The invention also relates to a preparation method for preparing a composition according to the invention.

According to one variant, the method typically includes:
- the dissolution of a substituted chitosan in an aqueous solution, preferably in a buffered solution, preferably having a pH comprised between 6.2 and 8.5, and preferably between 6.5 and 7.5;
- the optional adjustment of the pH to a desired pH, in general to the physiological pH for the targeted application, for example by adding a buffering agent, an acid or a base;
- the optional addition of other excipients, such as for example a reducing sugar, for example sorbitol or mannitol;
- the optional adjustment of the final osmolality of the composition.

Advantageously, the method also includes a further filling step for filling an injection or implantation device, such as for example a syringe, with the carboxyalkyl chitosan or the composition comprising the same. Advantageously, the injection device, such as for example a syringe, may then be subjected to a steam sterilisation process. This device, for example a syringe, may then be packaged, preferably in a sterile manner. It may also be a pouch, a vial, or a bottle that serves to enable the instillation of the carboxyalkyl chitosan solution.

It is advantageous to use a chitosan having a sufficient degree of purity for the intended application.

Advantageously, the method also includes a further filling step for filling an injection, implantation or instillation device, such as for example a syringe, with the composition according to the invention. Advantageously, the injection device, such as for example a syringe, may then be subjected to a steam sterilisation process. This device, for example a syringe, may then be packaged, preferably in a sterile manner.

According to one variant, the carboxyalkyl chitosan according to the invention is sterilised by filtration and/or by steam sterilisation, prior to the filling of an injection, implantation or instillation device, such as for example a syringe or a vial, therewith.

It is advantageous to use a chitosan having a sufficient degree of purity for the intended application.

The present invention relates more particularly to an injectable composition comprising the carboxyalkyl chitosan according to the invention.

The invention also relates to a pharmaceutical composition comprising at least one carboxyalkyl chitosan defined according to the invention.

According to one variant, the carboxyalkyl chitosan or the composition comprising the same is used as a pharmaceutical composition that is injectable, implantable or suitable for instillation, or a medical device that is injectable, implantable or suitable for instillation.

The invention also covers a carboxyalkyl chitosan or a composition comprising the same, in a dry form, in particular in a lyophilised form. It is possible in particular to (re)disperse, and preferably solubilise, the lyophilised product prior to use.

The present invention relates more particularly to a composition according to the invention for use in a therapeutic treatment, for example comprising the injection of the said composition, via a subcutaneous, intradermal, intraocular, or intra-articular route, for example for the repair, regeneration or filling in of at least one body tissue requiring repair or filling in.

Advantageously, according to one embodiment, a carboxyalkyl chitosan according to the invention exhibits the immunocompatibility of the formulations of fungal origin carboxymethyl chitosan with the use of the mouse air-pouch model, 24 hours after injection, and as expressed in the number of white blood cells being less than $10 \times 10^6$ cells/mL, and preferably less than $8 \times 10^6$ cells/mL.

Advantageously, according to one embodiment, a carboxyalkyl chitosan according to the invention exhibits the immunocompatibility of the formulations of fungal origin carboxymethyl chitosan with the use of the mouse air-pouch model, 24 hours after injection, and as expressed by a concentration of Interleukin 1 beta (IL1-beta) of less than $10 \times 10^{-9}$ g/mL, and preferably less than $5 \times 10^9$ g/mL.

Advantageously, according to one embodiment, a carboxyalkyl chitosan according to the invention exhibits the immunocompatibility of the formulations of fungal origin carboxymethyl chitosan with the use of the mouse air-pouch model, 24 hours after injection, and as expressed by a concentration of chemokine C—X—C motif ligand 1 (KC/CXCL1) of less than $50 \times 10^9$ g/mL, and preferably less than $30 \times 10^{-9}$ g/mL.

Advantageously, according to one embodiment, a carboxyalkyl chitosan according to the invention exhibits the immunocompatibility of the formulations of fungal origin carboxymethyl chitosan with the use of the mouse air-pouch model, 24 hours after injection, and as expressed by a concentration of Tumour Necrosis Factor alpha (TNF-alpha) of less than $150 \times 10^{-9}$ g/mL, and preferably less than $125 \times 10^{-9}$ g/mL.

Advantageously, according to one embodiment, a carboxyalkyl chitosan according to the invention exhibits the immunocompatibility of the formulations of fungal origin carboxymethyl chitosan with the use of the mouse air-pouch model, 24 hours after injection, and as expressed by a concentration of chemokine C—X—C motif ligand 1 (KC/CXCL1) of less than $50 \times 10^{-9}$ g/mL, and preferably less than $30 \times 10^9$ g/mL.

Advantageously, according to one embodiment, a carboxyalkyl chitosan according to the invention exhibits the immunocompatibility of the formulations of fungal origin carboxymethyl chitosan with the use of the mouse air-pouch model, 24 hours after injection, simultaneously satisfying the maximum limits expressed here above in terms of number of white blood cells and concentrations of IL1-beta, KC/CXCL1 and TNF-alpha.

The measurements of the number of white blood cells and of the concentrations of IL1-beta, KC/CXCL1 and TNF-alpha are carried out according to the protocols indicated in the examples.

Advantageously, according to one embodiment, a carboxyalkyl chitosan according to the invention has a half-life in the presence of a mixture of the enzymes lysozyme and hyaluronidase at 37° C. that is greater than 500 minutes, according to the measurement protocol in Example 6.

Advantageously, according to one embodiment, in particular in intra-articular application, a carboxyalkyl chitosan according to the invention has a coefficient of friction $(COF_0)$ of less than 5, and preferably less than or equal to 4 (according to the protocol in Example 9).

The present invention relates in particular to a composition according to the invention for use in a treatment in the areas of rheumatology, ophthalmology, aesthetic medicine, plastic surgery, internal surgery, for example for the prevention of post-surgical tissue adhesions, in cosmetic or dermatologic surgery.

According to one variant, the body tissue is selected from the tissues belonging to the vocal cords, muscles, ligaments, tendons, cartilages, sexual organs, bones, joints, eyes, dermis, epidermis, one or more layers of the skin, the mesoderm, or any one of the combinations thereof, and more particularly belonging to the eyes, the dermis and the articular joints.

The present invention also relates to a composition according to the invention for use in the therapeutic treatment of dry eye syndrome, corneal damage or injury, or joint inflammation.

The present invention in addition relates to the application of a composition according to the invention by means of instillation on the ocular surface in order to prevent or combat corneal damage or injury, or dry eye syndrome, in particular with a view to lubricating or regenerating the ocular surface.

Thus, the invention also relates to a composition of eye drops comprising a carboxyalkyl chitosan defined according to the present invention.

According to one variant, the subject is affected by an inflammatory pathology (eg osteoarthrosis).

The present invention relates more particularly to a composition according to the invention for the treatment of arthrosis (osteoarthritis), arthritis, or the repair of a cartilage defect, for example by means of injection into the synovial cavity or by implantation at the site of the cartilage defect.

The present invention relates more particularly to a medical device, for example medical implant, characterised in that it comprises or consists of a composition according to the invention.

According to one preferred variant, the invention therefore relates to a medical device comprising a chamber containing a carboxyalkyl chitosan in a dry form, in particular in a lyophilised form, and optionally one or more other chambers containing one or more active products, additives or excipients.

The composition according to the present invention may also comprise one or more additives or excipients that make it possible to modulate its properties.

The present invention also relates to a composition according to the invention for use in a therapeutic treatment method, for example comprising the instillation or the injection of the said composition, via a subcutaneous, intradermal, ocular, intraocular, or intra-articular route, for example for the repair or filling in of at least one body tissue requiring repair or filling in.

The present invention also relates to a composition according to the invention for the use thereof in a treatment method for treating osteoarthritis, or in the repair of a cartilage defect, for example by means of injection into the synovial fluid or after mixing with the blood and implantation in the cartilage.

The present invention also relates to a composition according to the invention for use in a method of treatment or method of aesthetic care rendered by filling the dermis ("dermal filling"). This in particular involves, for example, injecting a composition according to the invention subcutaneously or intradermally.

The present invention also relates to a composition according to the invention for use in a treatment method for surface treatment of the skin by means of multiple injections via the intradermal route. Such compositions may typically be used in dermatology, as treatments intended for aesthetic purposes. Such a method for example serves the purpose of plumping up the skin so as to cause it to lose its wrinkled appearance (treatment for wrinkles and/or fine lines). Such a treatment may be addressed to a subject who wishes to enhance their skin appearance with a rejuvenated look.

The present invention also relates to a composition according to the invention for use in a treatment method in which the composition is a viscosupplementation agent. In this case, for example, it involves the injecting of the composition of the invention in the intra-articular site in particular in order to limit the friction of the cartilage surfaces of the joint. The present invention also relates to a composition according to the invention for use as a cell vector, for one or more cell types, and/or one or more active agents. These may be active agents from a pharmaceutical or biological standpoint. The composition of the invention may in fact be compatible with the presence of cells, preferably living cells. Among the living cells of interest, mention may be made for example of: chondrocytes (articular cartilage), fibrochondrocytes (meniscus), ligament fibroblasts (ligament), skin fibroblasts (skin), tenocytes (tendons), myofibroblasts (muscle), mesenchymal stem cells, red blood cells (blood), and keratinocytes (skin). The composition of the invention may also be envisaged as a therapeutic vector for the targeted delivery and/or controlled release of at least one therapeutic agent.

According to one variant, the addition of blood, or plasma, or a platelet lysate, or platelet-rich plasma, or any biological fluid with the composition of the invention thereby makes it possible for example to enhance the performance aspects of the product.

According to one variant, the composition according to the invention is formulated in a solid form (for example a film or a porous foam), which is solubilised once it is implanted.

According to one variant, the composition is formulated in the form of a nebulisable (spray) composition.

The present invention also relates to a composition according to the invention for use in a method of treatment or method of aesthetic care for one or more tissues or organs affected by excessive temperature, as in the case of a burn.

The present invention also relates to a composition according to the invention for use in a cartilage treatment method for repairing a cartilage (for example by implantation on a cartilage defect in order to promote the regeneration of such cartilage.

The present invention also relates to a composition according to the invention for use in a treatment method for prevention of tissue adhesions after surgery: the product is applied on the tissues at the end of surgery, for example, gynecological surgery, abdominal surgery, etc.

The present invention also relates to a composition intended as an artificial synovial fluid, that comprises a carboxyalkyl chitosan according to the invention.

The composition according to the present invention provides the capability of mimicking a healthy synovial fluid or of improving a healthy or defective or degenerative synovial fluid by attempting, for example, to improve its lubricating capacity in order to reduce friction in the joint, and/or its shock absorption properties (identifiable by the modulus of elasticity G'), while being easily injectable for filling a syringe for example or for being injected into the human or animal body. For indicative purposes only, the modulus of elasticity G of healthy synovial fluid is comprised between 40 and 100 Pa, and its loss modulus G" is comprised between 1 and 10 Pa.

According to one variant, the carboxyalkyl chitosan, or the composition comprising the same, is injected in the form of a solution. Advantageously, according to this variant, the carboxyalkyl chitosan, or the composition comprising the same, is easily injectable through a fine needle, for example a needle with a 21 Gauge diameter, at ambient temperature. The term "easy" injection, is understood to indicate that preferably the force to be exerted on such a syringe so as to cause a composition according to the invention to flow through a 21 Gauge needle is less than 50 Newton, preferably a force less than 20 Newton.

The present invention also relates to a composition for application as artificial tears, that comprises a carboxyalkyl chitosan according to the invention.

In general, the ranges of osmolality and pH values sought in biomedical applications are close to the following ranges:

Osmolality:
Iso-osmolar with plasma: 285 to 295 mosm/kg;
Iso-osmolar with synovial fluid: 404±57 mosml/kg, according to "Clin Orthop Relat Res, 235, 289-95, 1988" and "Biochem Biophys Res Comm, 422, 455-461, 2012";
From 280 to 350 mosm/kg.

pH:
In general a physiological pH is above 6.8, in particular above 7.0, and in particular 7.4 (as for plasma or synovial fluid).

In general the pH of plasma is 7.4. In general the pH of the synovial fluid is 7.768+/−0.044 according to "J Bone Joint Surg Br, 41-B (2), 388-400, 1959"; or 7.3 according to "Acta Orthop Scand 634-641, 1969,", or also according to "Clin Rheumatol 25, 886-888, 2006".

In general the synovial pH in the case of osteoarthritis or arthritis is considered to be lower than that of healthy synovial fluid.

Thus, the present invention relates to a mixture of a synovial fluid with a composition according to the present invention, for example based on a volume ratio between (i) the carboxyalkyl chitosan, or the composition comprising the same, and (ii) the synovial fluid ranging from 20/80 to 80/20 (v/v), and for example being 50/50 (v/v).

Advantageously, the composition according to the present invention is sterile. Very advantageously, the composition according to the present invention is sterilised by raising the temperature, preferably in an autoclave.

According to one variant, the compositions of the invention are transparent or translucent.

The term "translucent" is understood to indicate that an object may be distinguished when the composition is placed between the eye of the observer and the said object. The term "transparent" Is understood to indicate that it is possible to distinguish alphanumerical characters when the composition is placed between the eye of the observer and the characters observed. In general, this evaluation is carried out with a composition of approximately 1 cm thickness. It is also possible to follow the method of monograph 2.9.20 of the European Pharmacopoeia, for visual inspection. It is also possible to measure the optical density of the composition, for example by means of UV-visible spectrometry at 500 nm and to ensure that the optical density is less than 0.5, preferably 0.2 in comparison with a reference solvent.

According to one variant, the compositions of the invention are not or only very slightly opalescent.

The term "opalescent" is understood to indicate that the solution results in a diffraction of light visible to the naked eye, for example by visual inspection according to a method such as in monograph 2.9.20 of the European Pharmacopoeia and by comparison with reference solutions having different levels of opalescence from the European Pharmacopoeia. According to one variant, the composition of the invention is colourless, that is to say in particular that an observer observing with the naked eye does not ascribe any specific colour to the composition. According to one variant, the opalescence is less than the maximum tolerable level for the intended application.

The invention relates in particular to articles or packaging, preferably sterile, comprising one or more instillation or injection devices pre-filled with a composition according to the invention. These are typically devices that enable the product to be instilled in the form of drops or in pre-filled syringes.

The composition of the invention may advantageously be sterilised. Thus, the invention relates to a sterilised carboxyalkyl chitosan. The carboxyalkyl chitosan is thus sterile, in particular for applications that require it.

According to one variant, the composition of the invention is steam sterilised, for example by raising the temperature to a temperature higher than 100° C., and preferably higher than 120° C., for example between 121° C. and 138° C., in an autoclave, for a period of time sufficient for sterilisation, for example in general from 15 to 20 minutes. According to another variant, the composition may be sterilised by means of filtration by using filters adapted for this purpose, for example filters with a porosity less than or equal to 0.2 μm.

Advantageously, according to one preferred embodiment, the loss in intrinsic viscosity of the carboxyalkyl chitosan during the steam sterilisation process is less than 40%.

The invention also covers a composition of the invention in a dry form, in particular in a lyophilised form.

It is possible in particular to (re)disperse this lyophilised composition prior to use.

The present invention also covers a therapeutic treatment method comprising the injection of a composition according to the invention.

The present invention also covers the use of a composition according to the invention for the preparation of a pharmaceutical composition, in particular for a therapeutic treatment, for example as defined more specifically by the invention.

The present invention also covers a method of aesthetic care, in other words non-therapeutic method, comprising the injection of a composition according to the invention. This involves for example the filling in of wrinkles or the filling in of one or more areas of damaged visible tissue, for example subsequent to an accident or a surgical intervention, for aesthetic purposes.

A tissue is a set of cells that are similar and having the same origin, grouped together as a functional unit, that is to say, contributing to the same given function. Among the tissues, mention may be made of: epithelial tissue, connective tissue, muscle tissue, and nervous tissue.

The term "composition according to the invention" or equivalent terms are understood to refer to a composition defined as in the present invention, including according to any one of the variants, particular or specific embodiments, independently of or according to any one of the combinations thereof, including according to the preferred characteristic features.

Other objects, characteristic features and advantages of the invention will become apparent to the person skilled in the art after reading the explanatory description which makes reference to examples which are given solely by way of illustration and which cannot in any way limit the scope of the invention.

The examples form an integral part of the present invention and any characteristic feature that appears to be novel as compared to any prior art document based on the description taken into consideration as a whole, including the examples, forms an integral part of the invention in respect of the function and generality thereof.

Thus, each example is general in scope.

On the other hand, in the examples, all of the percentages are given by mass, unless otherwise indicated, and the temperature is expressed in degrees Celsius unless otherwise indicated, and the pressure is atmospheric pressure, unless otherwise indicated.

EXAMPLES

The precursor chitosans of the substituted chitosans according to the invention have an average molecular mass in viscosity (determined by means of capillary viscosimetry) and a degree of acetylation (DA, proportion of N-acetyl-D-glucosamine unit, determined by means of potentiometric titration) comprised in the ranges in Table 1. The molecular mass of a chitosan may also be defined by the dynamic viscosity of a solution having a concentration of 1% (m/m) of chitosan in acetic acid having a concentration of 1% (v/v), as measured by means of a rotating spindle viscosimeter, for example a Brookfield viscometer, as described in Table 1.

TABLE 1

Characteristics of the precursor chitosans

| Range | Range of Average Molecular Mass (Capillary Viscosimetry) | Viscosity Range at 1% (mPa · s) | DA Range (mol %) |
|---|---|---|---|
| "Ultra low" | approx 20,000-60,000 | 5-20 | 5-20% |
| "Low" | approx 60,000-120,000 | 20-50 | 15-25% |
| "Medium" | approx 120,000-150,000 | 50-80 | 20-30% |
| "High" | approx 150,000-220,000 | 80-120 | 25-40% |
| "Ultra-high" | approx 220,000 to 300,000 | 120-200 | 25-40% |
| "400k" | approx 300,000-500,000 | 200-600 | 35-50% |

The following methods are used in the present invention, unless otherwise stated:

Method for Measuring the Zeta Potential

The formulation to be analysed is diluted in a phosphate buffer in order to obtain a final polymer concentration of 0.05%, then slightly agitated until homogenisation is achieved. The solution is then separated into different fractions, and the pH of each of the fractions is adjusted to the desired value, between pH 4 and 8, either by adding sodium hydroxide, 0.1N or by adding hydrochloric acid, 0.1N. The zeta potential of each fraction is measured using a "Nano-Z" device (Zeta-Sizer range, Malvern Instruments).

Method for Measuring the Solubility Range of Chitosan Polymers

The solubility range is established by preparing a solution of the polymer to be tested at a concentration of 1% and a pH of 9, by dividing it into several fractions of which the pH is adjusted to different pH values over a range of 9 to 1. For each fraction, the polymer is checked so as to ascertain that is soluble—that is to say that it does not form any turbidity—according to the visual inspection method of the monograph 2.9.20 of the European Pharmacopoeia. The pH range over which the polymer is soluble or insoluble is noted.

Mouse Subcutaneous Air-Pouch Model

A mouse subcutaneous air-pouch model was used in order to assess the foreign body reaction and immunocompatibility of various different polymers derived from the chitosan of fungal origin. In this model, an air-pouch cavity is produced by repeated subcutaneous injections of sterile air into the back of a mouse. The pouch generated by the inflation by the air mimics the synovial cavity, thus providing a localised environment in which it is possible to study the stimulation of an inflammatory response in the fluid withdrawn from the air-pouch and the surrounding tissues, such as is described by Segwick et al. (in: J Pathol 141, 483, 1983) and Sin et al. (in: Ann Rheum Dis 45, 873, 1986). The cavity of the air-pouch provides the means to inject up to 1 mL of product into an animal weighing approximately 30 g. According to the protocol described by Dawson et al. (in: Int J Tiss Reac 8, 171, 1991), the air-pouch is established in non-consanguineous male CD-1 Swiss albino mice (pathogen-free, body weight on reception 25 to 35 g) on a timeline of Day 0 and Day 4 by repeated injection of 5 mL and then 3 mL of sterile air. On Day 7, a single subcutaneous injection of 1 mL of product is administered directly into the air-pouch cavity. Injections of 1 mL of saline and a 1% solution of carrageenan serve as negative and positive controls, respectively. The animals are monitored regularly in the hours following the injection in order to detect possible clinical signs of systemic or local toxicity, and a gain in body weight and temperature is brought about at the time of injection and sacrifice. The animals are euthanised after a 24 hour period of contact with the product (3 animals per product). The immunological evaluations of the washing fluid recovered from the pouch include the cytological analysis (count and distribution of white and red blood cells) and the quantification of the main inflammatory mediators (IL-1-beta, TNF-alpha and KC/CXCL1) making use of 'ELISA' kits (AbCam), carried out according to the instructions. The macroscopic analysis and histopathology by means of hematoxylin/eosin staining of the surrounding skin tissues are carried out. Particular attention is paid to the localisation of the product on the surrounding tissues as well as resorption thereof in the fluid.

Model for Assessing Local Tolerance of Intra-Articular Administration in an Ovine Model According to the literature and the recommendations of the Osteoarthritis Research Society International (OARSI), sheep are recognised as being a well-characterised model for assessing the effects of intra-articular injection of innovative treatments (Little et al. In: Osteoarthritis Cartilage 18, S80, 2010; Edouard et al. In: Phys Ther Sport 14, 116, 2013; McCoy et al. In: Vet Pathol 52, 803, 2015). The sheep model provides the means for injection via intra-articular route of a volume of the formulation that simulates the clinical use of viscosupplementation in humans (Fraser et al. In: Semin Arthritis Rheum 22, 9, 1993). The measurements of local tolerability include clinical signs of synovial inflammation (effusion, lameness, comfort) by using validated semi-quantitative clinical scales, described by Shafford et al. (in: Vet Anaesth Analg 31, 20, 2004) and Kaler et al. (in: Vet J 180, 189, 2009), as well as the cytological evaluation of the synovial fluid. In some cases, these analyses may be supplemented by the anatomical and histological evaluation of the injected limb. A volume of 2 mL of formulation is injected into the joint (stifle) of healthy sheep (age 2 to 6 years; weight 60 to 80 kg). After injection, the clinical signs of the animals are recorded daily over a period of 15 days, based on a semi-quantitative scale from 0 to 4 for effusion (by palpation of the stifle) and lameness. The number of signs encountered for each of the scores over the entire observation period is reported. In order to evaluate the effects of a repeated injection of the same given formulation, a second injection is administered after 1 month in the joint of the same animals, and the animals are monitored according to the same protocol as for the first injection. In addition, a puncture of the synovial fluid is performed on day 15, and the macroscopic (colour, viscosity), cytological (count and distribution of white and red blood cells) parameters, as well as the amount of total serum proteins are determined according to conventional methods. The synovial fluid is considered normal if its appearance is clear, viscous and slightly yellowish, and the cytological analysis indicates that the number of white blood cells is less than $1 \times 10^5$ cells/mL and that the concentration of total proteins is approximately 25 mg/mL.

Example 1—N-Succinyl-Chitosans

The N-succinyl chitosans having different molecular mass and molecular structure (degree of acetylation (DA), and degree of substitution by the succinyl group (DS)) were prepared and characterised according to the general method described in the patent application WO 2016/016463 or WO 2016/016464 (patent EP 3016663). A first acetylation step by addition of acetic anhydride was carried out in order to increase the degree of acetylation, except for the polymer CSS-1 (Table 1a).

The formulations were prepared with these N-succinyl chitosans (CSS) at a concentration of 2% at physiological pH and osmolarity, and packaged in glass syringes. The syringes are sterilised by autoclave with a standard cycle (15 minutes at 121° C.). The formulations are checked so as to ascertain that they do not exhibit any insoluble matter or turbidity over a wide pH range around the physiological pH (pH 6.5 to 7.5), by visual inspection according to the method EP 2.9.20. It is checked that the level of bacterial endotoxins in the formulations is less than 20 EU/mL according to the method of monograph 2.6.14 (D) of the European Pharmacopoeia and that the microbiological load is less than 100 cfu/g according to method 2.6.12 of the European Pharmacopoeia, prior to carrying out an evaluation of their immunocompatibility in vivo.

TABLE 1a

Characteristics of N-succinyl chitosans

| No | Range of Molecular Mass | DA* (mol: %) | DS* (mol %) |
|---|---|---|---|
| CSS-1 | Medium | 12 | 62 |
| CSS-6 | Low | 50 | 34 |
| CSS-8 | Low | 49 | 32 |
| CSS-10 | High | 61 | 37 |

*molecular mass of the precursor chitosan, according to Table 1;
**DA and DS measured by proton NMR according to the method described in the patent EP 3016663.

The immunocompatibility of the CSS formulations is evaluated by means of the mouse subcutaneous air-pouch model (Table 1 b). The reaction observed is compared to the reaction observed after injection of a saline solution (negative control), a very reactive positive control (1% solution of carrageenan), and a commerciallly available product based on Hylan GF-20, partially cross-linked hyaluronic acid (Synvisc®, Sanofi).

TABLE 1b

Immunocompatibility of N-succinyl chitosan formulations using the mouse subcutaneous air-pouch model, 24 hours after injection*

| No | No of white blood cells ($10^6$ cell/mL) | Conc of IL1-beta ($10^{-9}$ g/mL)** | Conc of KC/CXCL1 ($10^{-9}$ g/mL) | Conc of TNF-alpha ($10^{-9}$ g/mL)** |
|---|---|---|---|---|
| CSS-1 | 1.5 | / | / | / |
| CSS-6 | 0.7 | <3 | 137 | <125 |
| CSS-8 | 3.7 | / | / | / |
| CSS-10 | 2.1 | <3 | >700 | <125 |
| Controls | | | | |
| Negative control (saline) | 0.2 | 17 | 23 | 272 |
| Positive control (1% carrageenan) | 33.2 | 28 | 700 | 767 |
| Synvisc ® (Hylan GF-20) | 0.7 | 4 | 46 | <125 |

*average value over 3 animals;
**detection limit: $3.10^{-9}$ g/mL for IL1-beta and $125.10^{-9}$ g/mL for TNF-alpha.

In general, it appears that these CSS-based formulations cause an immunological reaction of the foreign body reaction type, as evidenced by the number of white blood cells in the cell infiltrate being higher than for the negative control, however not as high as for the positive control (1% carrageenan). The reaction induced by the formulations is characterised by activation of the neutrophils, as evidenced by a higher concentration of the marker KC/CXCL1 than those for the negative control and for the Synvisc® product. As for the markers IL1-beta and TNF-alpha, the levels thereof are low.

Modifying the DA and/or the DS of the CSS or indeed modifying the molecular mass thereof does not result in any difference in immunological reaction. Although the CSS formulations do not cause any deleterious effect on the tissues locally, it is necessary to be able to obtain a higher level of immunocompatibility in the case of therapeutic applications which target tissues that are weakened by the underlying pathology concerned, for example such as dry eye syndrome, corneal damage or inflammation relating to joint pathologies.

Example 2—Carboxymethyl Chitosans of Animal Origin

It was possible to obtain two carboxymethyl chitosans of animal origin, for pharmaceutical or medical use that are implantable or injectable (CC-1 and CC-2 in Table 28).
Two other carboxymethyl chitosans were tested:
One CC obtained by carboxymethylation of chitin of animal origin (CC-3),
One CC obtained by carboxymethylation of chitosan of animal origin, the chitosan having been prepared by deacetylation of a chitin of animal origin (CC-4).

The carboxymethyl chitosans (CC) were characterised by carbon 13 NMR in order to confirm their identity and determine the values of DA (degree of acetylation) and DS (degree of substitution with the carboxymethyl group), with a margin of error estimated at approximately ±10% (Table 2a). The electrostatic charge of the polymer is characterised by measuring its zeta potential at a concentration of 0.05% (m/m) over a pH range going from pH 8 to pH 4, and the value of the zeta potential at pH 7.5 (Table 2a) is reported. It is observed that the value of the zeta potential at pH 7.5 is relatively well correlated with the value of the DS as determined by means of carbon 13 NMR. For example the polymer CC-3 is substituted to a greater extent than the polymer CC-4 by the anionic carboxymethyl group (in carboxylate form at pH 7.5) and has a similar DA, therefore its overall negative charge is greater (−28 mV vs −11 mV at pH 7.5).

It is observed that the polymers CC-1 and CC-2 are not very soluble in the physiological pH range (pH 6.5 to 7.5). It is not possible to assess their immunocompatibility by using the mouse subcutaneous air-pouch model. The polymers CC-3 and CC-4 are indeed soluble over the entire wide pH range, of 1 to 9.

TABLE 2a

Characteristics of carboxymethyl chitosans of animal origin and the formulations thereof

| No (concentration) | DA* (mol %) | DS* (mol %) | Solubility range of the polymer | Sterilisability of the formulation by autoclave | Zeta potential at pH 7.5 (mV) |
|---|---|---|---|---|---|
| CC-1 (2%) | 8 | 124 | Insoluble between pH 3.6 and 8.1 | / | / |
| CC-2 (2%) | / | / | Insoluble at pH below 6.6 | / | / |
| CC-3 (2%) | 71 | 149 | Soluble at all pH values | No | −28 |
| CC-4 (1.5%) | 69 | 24 | Soluble at all pH values | Yes | −11 |

*the DA and DS values of the carboxymethyl chitosan polymers are determined by solid-state carbon-13 nuclear magnetic resonance (NMR) spectroscopy.

The CC-3 (2%) and CC-4 (1.5%) formulations were then prepared according to the same method as that of Example 1, packaged in glass syringes and then sterilised by autoclave according to a standard cycle of 15 minutes at 121° C. (Table 2a). It is found that the 2% formulation of the polymer CC-3 does not withstand final sterilisation by autoclave, as evidenced by a loss in its intrinsic viscosity of approximately 60% reflecting the hydrolysis of the polymer, as well as by a 98% loss in its storage modulus G'. As an alternative to final autoclave sterilisation, the formulation CC-3 is then filtered prior to being packaged in a syringe in order to produce a formulation which can be evaluated by making use of the mouse air-pouch model.

The formulations of CC-3 (2%, filtered) and CC-4 (1.5%, sterilised by autoclave) are checked so as to ascertain that the level of endotoxins and the microbiological load are lower than 20 EU/mL and 100 cfu/g, and then their immunocompatibility is evaluated by making use of the mouse subcutaneous air-pouch model (Table 2b).

TABLE 2b

Immunocompatibility of formulations of carboxymethyl chitosan of animal origin using the mouse subcutaneous air-pouch model, 24 hours after injection*

| No | No of white blood cells ($\times 10^6$ cells/mL) | Conc of IL1-beta ($\times 10^{-9}$ g/mL)** | Conc of KC/CXCL1 ($\times 10^{-9}$ g/mL) | Conc. TNF-alpha ($\times 10^{-9}$ g/mL)** |
|---|---|---|---|---|
| CC-3 | 0,7 | <3 | 49 | <125 |
| 4 | 1,0 | 5 | 115 | 184 |
| Controls | | | | |
| Negative control (saline) | 0.2 | 17 | 23 | 272 |
| Positive Control (1% carrageenan) | 33.2 | 28 | >700 | 767 |
| Synvisc ® (Hylan GF20) | 0.7 | 4 | 46 | <125 |

*average value over 3 subjects;
**detection limit: $3.10^{-9}$ g/mL for IL1-beta and $125.10^{-9}$ g/mL for TNF-alpha.

The formulation of CC-4 causes a significant reaction, characterised by a high concentration of the two markers KC/CXCL1 (activation of neutrophils) and TNF-alpha in the infiltrate, simultaneously. The marker TNF-alpha was not detected after injection of the CSS formulations described in Example 2 or Synvisc® (Hylan GF-20). However, it is not desirable to induce a reaction characterised by the marker TNF-alpha. As it is desired to have good immunocompatibility in the case of therapeutic applications for which the formulation is expected to be in contact with tissues that are weakened by the underlying pathology, such as for example dry eye syndrome, corneal damage or injury, or articular inflammations, and to avoid activation of neutrophils and TNF-alpha, the carboxymethyl chitosan of animal origin CC-4 is not suitable.

The formulation CC-3 induces a lower reaction, characterised by a number of white blood cells and a moderate concentration of the marker KC/CXCL1, similar to the levels of the comparator product Synvisc® but higher than that of the negative control (saline). The CC-3 formulation therefore appears to be less immunoreactive than the CSS formulations and the CC-4 formulation. However, the CC-3 formulation presents the disadvantage of having a concentration of the marker KC/CXCL1 which could prove to be unsuitable for a therapeutic treatment method where the subject requires very good immunocompatibility, and of undergoing very significant hydrolysis of the macromolecular chains under the effect of heat, which thus renders impossible the sterilisation thereof by autoclave during a final step at the end of the production process, that is to say after filling of the syringe with the formulation.

Example 3—Carboxymethyl Chitosans of Fungal Origin

In order to obtain the carboxymethyl chitosans of Tables 3a and 3b starting from chitin or chitosan of fungal origin, the following reactions are carried out:

Reacetylation followed by carboxymethylation of fungal chltosan with "Ultra-high" molecular mass (CC-5 of Table 3a);

Carboxymethylation followed by reacetylation of fungal chitosan with "ultra-high" molecular mass (CC-5 to CC-9);

Carboxymethylation of fungal chitosan with "ultra-high" molecular mass (CC-11);

Carboxymethylation of fungal chitin (CC-10).

By way of example, the preparation of CC-8 takes place in the following manner: 10 g of "ultra-high" chitosan are dispersed in 220 ml of isopropanol and 68 ml of 40% sodium hydroxide (m/v). 45 g of the alkylating agent monochloroacetic acid (MCA) are dissolved in 45 ml of isopropanol, and added to the suspension of chitosan. The reaction is allowed to continue for a period of 16 hours at 25° C. The polymer is recovered by precipitation in ethanol, then purified by cycles of solubilisation/precipitation in ethanol. The precipitate is dried in a ventilated oven. A mass of 15 g of the precipitate is dispersed in water, and 3.75 ml of acetic anhydride are added thereto. After 30 minutes of agitation at ambient temperature, the pH of the medium is adjusted to 6, and 3.75 ml of acid anhydride (AC) are added thereto. After 30 minutes of agitation at ambient temperature, the medium is neutralised and precipitated in ethanol. The precipitate thus obtained is redissolved and then precipitated again. The final precipitate of carboxymethyl chitosan (CC-8) is dried in a ventilated oven.

The parameters of synthesis applied to prepare the other CCs are described in Tables 3a and 3b.

TABLE 3b-continued

Parameters for the synthesis of carboxyalkyl chitosan starting from fungal chitin

| Parameters | CC-10 |
|---|---|
| Duration and temperature of reaction | 16 hours at 25° C. |

The carboxymethyl chitosans (CC) of fungal origin obtained are characterised by carbon 13 NMR in order to confirm their structure and determine the value of the DA and the DS (Table 3c). Taking into account the standard deviation inherent in the carbon 13 NMR spectrometry method (approximately ±10%), it is observed that the value of the zeta potential at pH 7.5 is correlated with the molecular structure, in particular with the DS.

TABLE 3c

Characteristics of the carboxymethyl chitosans of fungal origin and the formulations thereof

| No (concentration) | DA* % | DS* % | Solubility of the polymer | Sterilisable by autoclave** | Zeta Potential at pH 7.5 (mV) |
|---|---|---|---|---|---|
| CC-5 (1.5%) | 67 | 18 | Soluble at any pH | Yes | −12.5 |
| CC-6 (2%) | 71 | 42 | Soluble at any pH | Yes | −15 |

TABLE 3a

Parameters for the synthesis of carboxyalkyl chitosan starting from fungal chitosan

| Parameters | CC-5 | CC-6 | CC-7 | CC-8 | CC-9 | CC-11 |
|---|---|---|---|---|---|---|
| Carboxymethylation step | | | | | | |
| Alkylating agent (MCA or SCA)* | SCA | MCA | MCA | MCA | MCA | MCA |
| NaOH/chitosan (m/m) | 11 | 2.7 | 2.7 | 2.7 | 2.7 | 2.7 |
| Urea | Yes | No | No | No | No | No |
| Alkylating agent/chitosan (m/m) | 11.2 | 9 | 9 | 4.5 | 4.5 | 6.8 |
| Isopropanol/alkylating agent (%, m/m) | 0% | 80% | 80% | 80% | 80% | 80% |
| Temperature (° C.) | 15° C. | 15° C. | 25° C. | 25° C. | 35° C. | 60° C. |
| Duration (hours) | 22 hr | 16 hr | 16 hr | 16 hr | 4 hr | 1 hr |
| Reacetylation step | | | | | | |
| Before or after carboxymethylation | before | after | after | after | after | / |
| AC/chitosan (v/m) | | | | | | |
| First addition | 0.3 | 0.25 | 0.25 | 0.25 | 0.25 | / |
| Second addition | 0.3 | 0.25 | 0.25 | 0.25 | 0.25 | / |
| Duration and temperature of reaction | 0.5 hour at 25° C. | 0.5 hour at 25° C. | 0.5 hour at 25° C. | 0.5 hour at 25° C. | 0.5 hour at 25° C. | / |

*MCA: monochloroacetic acid; SCA: sodium salt of monochloroacetic acid.

TABLE 3b

Parameters for the synthesis of carboxyalkyl chitosan starting from fungal chitin

| Parameters | CC-10 |
|---|---|
| Chitin/soda/water (m/m) | 1/11.4/28.5 |
| Duration and temperature of contact with soda | 16 hours at 4° C. |
| Alkylating agent (MCA or SCA) | MCA |
| Chitin/isopropanol/alkylating agent (m/m/m) | 1/28.5/4.5 |

TABLE 3c-continued

Characteristics of the carboxymethyl chitosans of fungal origin and the formulations thereof

| No (concentration) | DA* % | DS* % | Solubility of the polymer | Sterilisable by autoclave** | Zeta Potential at pH 7.5 (mV) |
|---|---|---|---|---|---|
| CC-7 (2%) | 57 | 70 | Soluble at any pH | Yes | −18 |
| CC-8 (2%) | 50 | 80 | Soluble at any pH | Yes | −26 |

TABLE 3c-continued

Characteristics of the carboxymethyl chitosans of fungal origin and the formulations thereof

| No (concentration) | DA* % | DS* % | Solubility of the polymer | Sterilisable by autoclave** | Zeta Potential at pH 7.5 (mV) |
|---|---|---|---|---|---|
| CC-9 (2%) | 41 | 101 | Soluble at pH >3.1 | Yes | −22 |
| CC-10 (2%) | 46 | 167 | Soluble at any pH | Yes | −24.5 |
| CC-11 (2%) | 23 | 130 | Soluble at pH >3.5 | Yes | −26 |

*DA and DS as determined by 13C-NMR;
**considered sterilisable if the loss in intrinsic viscosity before/after sterilisation is less than 40%.

The CC obtained are all soluble over a wide pH range, in particular over the pH range of 4.0 to 8.5, without opalescence.

The formulations are prepared at a CC concentration of 1.5 or 2%, packaged in glass syringes, then sterilised by autoclave according to a standard 15-minute cycle at 121° C. In order to evaluate whether the formulations are sterilisable by autoclave, the intrinsic viscosity of the polymers is measured before and after autoclaving by capillary viscosimetry, after dilution by a factor of 25 with a phosphate buffer. The loss in intrinsic viscosity of the CC is less than 40%, which indicates an acceptable resistance, contrary to the CC-3 formulation described in Example 2 (which underwent a loss of approximately 60% in its intrinsic viscosity).

Visual inspection of the sterilised formulations included in Table 3c indicates that they are transparent and not opalescent. They are then checked so as to ascertain that the level of endotoxins and the microbiological load are less than 20 EU/mL and 100 cfu/g, and thereafter their immunocompatibility is evaluated by making use of the mouse subcutaneous air-pouch model.

It is noted that a low concentration of the marker KC/CXCL1 is induced by the formulations of CC of fungal origin, at the same level as that for the negative control (saline) and lower than that for the product Synvisc®. This reflects negligible or even absent neutrophil activation, contrary to the level that has been reported after injection of the formulations of CSS (Example 1) and of CC of animal origin (Example 2).

Furthermore, it is noted that for certain of the formulations of CC of fungal origin (ie CC-8 and CC-10), the four parameters of the immune reaction are attenuated or suppressed simultaneously, that is to say both the total number of white blood cells, the marker IL1-beta, the marker KC-CXCL1 and the marker TNF-alpha. This does not happen with the CSS formulations or with the formulations of CC of animal origin.

It appears that for the CCs of fungal origin, the formulations which exhibit this simultaneous attenuation of the four parameters are those with the highest negative charge (eg −26 my for CC-8 and −24.5 mV for CC-10 at pH 7.5).

It is observed that the formulations of CC-4 of animal origin described in Example 2 and of CC-5 of fungal origin weakly substituted by the carboxyalkyl group, cause a certain activation of the marker TNF-alpha, and that on the other hand only the formulation of CC-4 of animal origin leads to a significant secretion of the marker KC/CXCL1. It is also observed that the formulation of CC-10 (of fungal origin) did not result in activation of the neutrophils, unlike the formulation of CC-3 of animal origin described in Example 2.

Example 4—Evaluation of the Local Tolerance of Intra-Articular Administration of Formulations of Fungal Origin Carboxymethyl Chitosan Using an Ovine Model Formulations with 2% of two carboxymethyl chitosan of fungal origin (CC-8 and CC-10) described in Example 3 are TABLE 3d Immunocompatibility of the formulations of fungal origin carboxymethyl chitosan using the mouse subcutaneous air-pouch model, 24 hours after injection*

| No | No of white blood cells ($\times 10^6$ cells/mL) | Conc of IL1-beta ($\times 10^{-9}$ g/mL) | Conc of KC/CXCL1 ($\times 10^{-9}$ g/mL) | Conc of TNF-alpha ($\times 10^{-9}$ g/mL)** |
|---|---|---|---|---|
| CC-5 | 1.9 | 6 | 28 | 391 |
| CC-6 | 17 | 12 | 20 | <125 |
| CC-7 | 9.0 | 12 | 20 | <125 |
| CC-8 | 2.6 | <3 | 20 | <125 |
| CC-9 | 6.5 | 7 | 20 | <125 |
| CC-10 | 2.4 | <3 | 16 | <125 |
| Controls | | | | |
| negative control (saline) | 0.2 | 17 | 23 | 272 |
| positive Control (1% carrageenan) | 33.2 | 28 | >700 | 767 |
| Synvisc ® (Hylan GF20) | 0.7 | 4 | 46 | <125 |

*average value over 3 subjects;
**detection limit: $3.10^{-9}$ g/mL for IL1-beta and $125.10^{-9}$ g/mL for TNF-alpha.

In general, it is noted that there is good immunocompatibility of the CC formulations of fungal origin, with an attenuation or even a suppression of the immune reaction as compared to the formulations of N-succinyl chitosan described in Example 1 and to the formulations of carboxymethyl chitosan of animal origin described in Example 2.

prepared in order to assess their potential for use via intra-articular injection, by means of an ovine (sheep) model. A volume of 2 mL of the two formulations is administered to the sheep, and the local reaction induced by the intra-articular injection thereof is evaluated over a period of 2 weeks. The effects of a second injection of the CC-8 formulation in the same joint, 1 month after the date of the first injection, were also evaluated. The product Synvisc® is administered in the same manner, with a volume of 1 mL or 2 mL.

The clinical signs are monitored daily by palpation of the joint and observation of lameness over a period of 15 days and judged on the basis of a semi-quantitative score of 0 (no signal) to a maximum score of 3 for effusion and 5 for lameness. The overall clinical result over the period of 15 s is reported in terms of incidence by score (Table 4), as well as the characterisation of the synovial fluid produced on day 15.

TABLE 4

Evaluation of the local tolerance of formulations of fungal origin carboxymethyl chitosan and Synvisc ® using a sheep model, by intra-articular injection

| Formulation No Volume (N: no of animals) | Incidence of effusion over 15 days (score 0 to 3) | Incidence of lameness over 15 days (score 0 to 5) | Characterisation of the synovial fluid punctured on day 15 |
|---|---|---|---|
| CC-8 First injection of 2 mL (N = 4) | Score 0: 100% Scores 1 to 3: 0% | Score 0: 100% Scores 1 to 5: 0% | Normal |
| CC-8 Second injection of 2 mL (N = 2) | Score 0: 100% Scores 1 to 3: 0% | Score 0: 100% Scores 1 to 5: 0% | Normal |
| CC-10 One injection of 2 mL (N = 4) | Score 0: 100% Scores 1 to 3: 0% | Score 0: 100% Scores 1 to 5: 0% | Normal |
| Synvisc ® (Hylan GF-20) N = 8, of which: one injection of 1 mL (N = 4), one injection of 2 mL (N = 4) | Score 0: 62.5% Score 1: 37.5% Scores 2 to 3: 0% | Score 0: 62.5% Score 1: 37.5% Scores 2 to 5: 0% | Normal |

Example 5—Evaluation of the Local Tolerance of Formulations of Fungal Origin Carboxymethyl Chitosan after Intradermal Injection in Rabbits Formulations of three carboxymethyl chitosans of fungal origin at physiological pH and osmolality are prepared with a view to evaluating their potential for intradermal administration, by making use of a rabbit model (Table 5a). The CC-12, CC-13, CC-14 and CC-15 of fungal origin are prepared by means of carboxymethylation, then followed by reacetylation according to the general method described in Example 3 for CC-8, while modulating the parameters of synthesis so as to cause to vary the DA and the DS (Table 5a). CC-13 and CC-14 present a low DS of 41% and 51% respectively, and a high DA of 74% and 69% respectively.

The formulations are packaged in a 1 ml glass syringe, and then sterilised by autoclave according to a standard cycle (15 minutes at 121° C.). The three formulations are resistant to the autoclave sterilisation, the loss of intrinsic viscosity being less than 40%. Finally, the formulations are checked so as to ascertain that the level of bacterial endotoxins is less than 40 EU/mL and the microbiological load is less than 100 cfu/mL.

A volume of 200 µL of formulation is administered to rabbits by intradermal injection via a needle with 27 Gauge diameter (needle with very small diameter), according to a protocol that is compliant with the standard ISO10993 (part 10) for the evaluation of primary irritation induced by an intradermal implant. A number of six rabbits each receive three injections of each formulation. A commercially available dermal filler product based on cross-linked hyaluronic acid, Juvéderm® Voluma (Allergan), is also injected via a 27 Gauge diameter needle. Macroscopic signals of skin irritation are reported for all the animals and sites injected at 12, 24 and 48 hours with a view to determining the primary irritation score, by assessing the possible appearance of erythema, eschar, edema and induration on a semi-quantitative scale, based on a score of 0 (no signal) to 4 (maximum signal). The primary irritation score for each product is determined in the following manner: the average of the erythema scores of the 18 sites injected at 24, 48 and 72 hours is added. The sum of the averages of the edema score is calculated in the same manner. The 2 sums (erythema and edema) are added, and then divided by 54 in order to obtain the mean primary irritation score. The same procedural approach is followed with the comparator product. The irritation scores are reported in Table 5b. It is observed that the CC formulations produced no signs of edema and few signs of erythema, with a score lower than those induced by Juvéderm® Voluma in all the cases. It is concluded that the formulations are non-irritating and less irritating than Juvéderm® Volume.

TABLE 5a

Characteristics of the fungal origin carboxymethyl chitosans and formulations thereof

| No (concentration) | DA* (mol %) | DS* (mol %) | Solubility of the polymer | Sterilisable by autoclave** | Zeta Potential at pH 7.5 (mV) |
|---|---|---|---|---|---|
| CC-12 (3%) | 41 | 50 | Insoluble between pH 3.1 and 6.6 | Yes | −17 |
| CC-13 (3%) | 74 | 45 | Soluble at any pH | Yes | −20 |
| CC-14 (3%) | 69 | 51 | Soluble above pH 3.6 | Yes | −17*** |
| CC-15 (2%) | 55 | 100 | Soluble above pH 3.1 | Yes | −27.5 |

*as determined by 13C-NMR;
**considered sterilisable if the loss in intrinsic viscosity before/after sterilisation by autoclave is less than or equal to 40%;
***value estimated from the polynomial regression of the zeta potential curve at pH 7.5 as a function of the DS (±20%).

TABLE 5b

Evaluation of the primary irritation score of formulations of carboxymethyl chitosan and Juvéderm ® Voluma after intradermal injection in rabbits

| No (concentration) | Primary irritation score at 72 hours Total score (and mean score) |
|---|---|
| CC-12 (3%) | 0.11 (0.002) |
| CC-13 (3%) | 0.22 (0.004) |
| CC-13 (3%) | 0.17 (0.003) |
| CC-14 (2%) | 0 (0) |
| Juvéderm ® Voluma | 2.67 (0.049) |

The observation period is then extended to 2 weeks after injection, with an evaluation of the clinical signals on days 5, 7, 9, 11 and 14. In order to carry out a possible histological analysis, 2 animals are sacrificed on Day 3, Day 7 and Day 14 after injection. The gross scores are reported in Table 5c. It is observed that the four formulations exhibit excellent local tolerance over a period of 2 weeks after intradermal injection, with scores that are lower than those observed with the product Juvéderm® Voluma for all gross or macroscopic signs, and no signs of eschar or edema. The CC-12 and CC-13 formulations show some signs of low score erythema (1 maximum) which disappeared on Day 11. The CC-13 formulation shows some signs of erythema with maximum score 2, with a 33% incidence on Day 9, which also disappeared on Day 11 and did not result in a deleterious effect on the tissue.

TABLE 5c

Evaluation of the local tolerance of formulations of carboxymethyl chitosan after intradermal injection in rabbits (2 weeks) (expressed in terms of incidence of scores)

| No (concentration) | Time frame (no of sites)* | Day 3 (18) | Day 5 (12) | Day 7 (12) | Day 9 (6) | Day 11 (6) | Day 14 (6) |
|---|---|---|---|---|---|---|---|
| Erythema score | | | | | | | |
| CC-12 (3%) | Score 0-1 | 100% | 100% | 100% | 100% | 100% | 100% |
| | Score 2-4 | 0% | 0% | 0% | 0% | 0% | 0% |
| CC-13 (3%) | Score 0-1 | 100% | 100% | 83% | 67% | 100% | 100% |
| | Score 2-4 | 0% | 0% | 17% | 33% | 0% | 0% |
| CC-14 (3%) | Score 0-1 | 100% | 100% | 100% | 100% | 100% | 100% |
| | Score 2-4 | 0% | 0% | 0% | 0% | 0% | 0% |
| CC-15 (2%) | Score 0-1 | 100% | 100% | 100% | 100% | 100% | 100% |
| | Score 2-4 | 0% | 0% | 0% | 0% | 0% | 0% |
| Juvéderm ® Voluma | Score 0-1 | 6% | 17% | 17% | 17% | 33% | 33% |
| | Score 2-4 | 94% | 83% | 83% | 83% | 67% | 67% |
| Eschar and Edema Scores | | | | | | | |
| CC-12 (3%) | Score 0-1 | 100% | 100% | 100% | 100% | 100% | 100% |
| | Score 2-4 | 0% | 0% | 0% | 0% | 0% | 0% |
| CC-13 (3%) | Score 0-1 | 100% | 100% | 83% | 67% | 100% | 100% |
| | Score 2-4 | 0% | 0% | 17% | 33% | 0% | 0% |
| CC-14 (3%) | Score 0-1 | 100% | 100% | 100% | 100% | 100% | 100% |
| | Score 2-4 | 0% | 0% | 0% | 0% | 0% | 0% |
| CC-15 (2%) | Score 0-1 | 100% | 100% | 100% | 100% | 100% | 100% |
| | Score 2-4 | 0% | 0% | 0% | 0% | 0% | 0% |
| Juvéderm ® Voluma | Score 0-1 | 100% | 100% | 100% | 100% | 100% | 100% |
| | Score 2-4 | 0% | 0% | 0% | 0% | 0% | 0% |

*number of sites macroscopically evaluated at each time frame after injection. Furthermore, the four compositions (CC-12, CC-13, CC-14 and CC-15) can be easily injected through a fine 27 Gauge needle, suitable for intradermal administration.

Example 6—Susceptibility to Enzymatic Degradation In Vitro

In this example, a comparison is done of the speed at which a formulation is degraded in the presence of a mixture of the two enzymes lysozyme and hyaluronidase present in biological fluids (for example synovial fluid, tears or the interstitial fluid of connective tissues). The enzyme lysozyme is generally recognised for its ability to hydrolyse chitosan-based biomaterials.

A fungal carboxymethyl chitosan CC-16 is prepared in the same manner as the CC-8 indicated in Example 3, by modulating the parameters of synthesis in order to adjust the DA and the DS. The 2% formulations of CC-16, CC-8 (Example 3) and CC-10 (Example 3) are prepared in phosphate buffer with 3.5% sorbitol. An assessment is also performed of a 2% formulation of CC-3 of animal origin (Example 2) and two commercially available viscosupplementation products based on non-crosslinked hyaluronic acid (HA-1 and HA-2).

The formulation is diluted by a factor of 25 in a phosphate buffer. The solution is then agitated for a period of 12 hours and a mixture of the enzymes lysozyme and hyaluronidase is added to the diluted solution, at doses of 184 units/mL and 2.6 units/mL, respectively. The measurement of intrinsic viscosity is carried out at regular intervals, by means of an automatic capillary viscometer I-Visc (Lauda) equipped with an Ubbelohde type capillary (model 0a). The half-life of each formulation, that is to say the time needed for the intrinsic viscosity of the polymer to reach half of its initial value, is then calculated (Table 6).

TABLE 6

Half-life of the formulations in the presence of a mixture of the enzymes lysozyme/hyaluronidase at 37° C.

|  | CC-8 (2%) | CC-10 (2%) | CC-16 (2%) | CC-3 (2%) | HA-1 | HA-2 |
|---|---|---|---|---|---|---|
| DA/DS (mol %)* | 50/80 | 46/167 | 67/115 | 71/149 | / | / |
| half-life (minutes) | 1200 min | 958 min | 612 min | 88 min | 73 min | 11 min |

*as determined by solid-state carbon-13 nuclear magnetic resonance (NMR) spectroscopy.

It is understood from the results that the formulations of carboxymethyl chitosan are hydrolysed by the lysozyme/hyaluronidase mixture, and that the kinetics of hydrolysis may be modulated via the molecular structure of the carboxymethyl chitosan. This makes it possible to adjust the duration of residence of the product according to the targeted therapeutic application. It is also inferred therefrom that the carboxymethyl chitosans of fungal origin are less rapidly degraded than the carboxymethyl chitosan of animal origin (CC-3) as well as the two commercially available products based on hyaluronic acid.

Example 7—Impact of Heat

In this example, the syringes containing the formulations are placed in an oven at temperature controlled at 60° C. for a period of 11 days, which makes it possible to assess their resistance to heat at a temperature that is higher than the usual storage temperature. At each time frame, a syringe is withdrawn and the intrinsic viscosity of the polymer is measured according to the method described in Example 6. The ratio between the viscosity at the given time frame and the initial viscosity is reported (in % of the initial viscosity).

Two carboxymethyl chitosans of fungal origin, CC-17 and CC-18, are prepared in the same way as the CC-8 of Example 3, by modulating the parameters of synthesis so as to adjust the DA and the DS, and characterised by means of Carbon 13 NMR (Table 7). They are formulated at a concentration of 2% in the presence of a reducing sugar, sorbitol or mannitol, respectively. An assessment is also performed of a 2% formulation of the CC-3 of animal origin indicated in Example 2 (with 3.5% of sorbitol), as well as the commercially available viscosupplementation product based on non-crosslinked hyaluronic acid indicated in Example 6 (HA-2).

TABLE 7

Change in the intrinsic viscosity of the formulations stored at 60° C. (in % of the initial intrinsic viscosity)

| No (concentration, reducing sugar) | DA/DS (mol %)* | Day 3 | Day 7 | Day 11 |
|---|---|---|---|---|
| CC-17 (2%, 3.5% sorbitol) | 71/49 | 96% | 95% | 91% |
| CC-18 (2%, 3.5% mannitol) | 71/49 | 100% | 92% | 91% |
| CC-3 (2%, 3.5% sorbitol) | 71/149 | 84% | 80% | 70% |
| HA-2 | / | 94% | 92% | 81% |

*as determined by solid-state carbon-13 nuclear magnetic resonance (NMR) spectroscopy It is concluded that the formulations of fungal origin carboxymethyl chitosan are resistant to heat, and are less sensitive than both the formulation of animal origin (CC-3) as well as a commercially available hyaluronic acid based product.

Example 8—Methods for Reducing the Microbiological Load of Carboxymethyl Chitosan A carboxymethyl chitosan of fungal origin, CC-19, is produced according to the method used to prepare the CC-8 of Example 3, starting from an "ultra-high" chitosan. Its characteristics are as follows: DA 67% and DS 115% (as measured by carbon 13 NMR), soluble at any pH, transparent, non-opalescent. The zeta potential at pH 7.5 of the formulation is estimated at −27 mV (from the polynomial regression of the zeta potential curve as a function of the DS). A 2% CC-19 formulation in a phosphate buffer with 3.5% sorbitol is prepared, as described in Example 3. Its characteristics are as follows: pH 7.3 and osmolality 279 mOsm/kg. In order to test their feasibility and the impact on the final characteristics of the formulation, two known methods are effectively implemented in order to reduce the microbiological load of aqueous formulations, and the intrinsic viscosity of the formulation (diluted by a factor of 25), is compared by making use of an I-Visc capillary viscometer (Lauda, capillary 0a) and its refractive index measured by making use of an HI88713 refractometer (Hanna) before and after the process (Table 8). The two methods are as follows:
- Autoclave: the formulation is placed into a glass syringe, and then the syringe is autoclaved according to a standard process (15 minutes at 121° C.);
- Filtration: a volume of 300 mL of formulation is filtered by using a 0.2 μm porosity filtre (Preflow capsule filtre, Pall).

The filtration process on a 0.2 μm filtre takes place in an appropriate manner, with a constant pressure of 2 bars and a constant flow rate of approximately 6 litres per hour.

TABLE 8

Impact of the filtration and autoclave methods on the 2% CC-19 formulation

| Indicator | Filtration method (0.2 μm) | Autoclave method (15 min 121° C.) |
|---|---|---|
| Difference in intrinsic viscosity (%) | 14% reduction in initial viscosity | 20% reduction in intrinsic viscosity |
| Difference in refractive index | No difference | No difference |

We conclude that the two methods have a low impact in terms of reduction of material (refractive index) and degradation of the polymer (intrinsic viscosity). They are therefore applicable industrially in order to obtain medical devices and pharmaceutical products based on the carboxymethyl chitosan formulations.

Example—9 Lubricating Capacity of the Formulations of Fungal Origin Carboxymethyl Chitosan, In Vitro This example seeks to illustrate the lubricating capacity of formulations of two carboxymethyl chitosans of fungal origin, CC-8 indicated in Example 3 (2% and 1%) and CC-19 indicated in Example 8 (2%), with a view to possible use thereof as an intra-articular viscosupplement or as an ophthalmic drop for the ocular surface. The lubricating capacity is evaluated by making use of an in vitro model which makes it possible to assess the reduction in friction between two surfaces. The formulation of CC-3 (2%) of animal origin indicated in Example 2 and the commercially available products based on hyaluronic acid are also characterised:

Intra-articular viscosupplements: Synvisc® (Sanofi) and two viscosupplements based on non-crosslinked hyaluronic acid, HA-2 indicated in Examples 6 and 7) and HA-3.

Eye drops: two products based on non-crosslinked hyaluronic acid (HA-4 and HA-5)

In addition, the synovial fluid sample is taken from the knee of a patient suffering from osteoarthrosis, prior to a surgical procedure for the placement of a knee prosthesis. The fluid is stored at −20° C., then brought to 25° C. prior to the analysis of the coefficient of friction.

The coefficient of friction is measured according to the following method. Two discs made from a polyacrylate type biomaterial used for the manufacture of hydrophobic intraocular lenses (as described in the patent EP 1830898), having a diameter of 16.15 mm, are hydrated in advance by immersion in water at 60° C. for a period of approximately 2 hours, then fixed to the upper and lower geometries of a Discovery Hybrid Rheometer-2 (DHR-2) (TA Instruments). A volume of approximately 100 μL of the fluid to be tested is placed on the lower disc, then the upper geometry is lowered until contact is brought about between the two discs, up to an imposed normal force of 5 Newton. The measurements of coefficient of friction are carried out at 25° C. for a period of 150 seconds, at constant normal force (5 N), oscillation frequency of 1.256 rad/s and angle of deformation of approximately 0.05 radians, according to a protocol adapted from the protocol described by Waller et al. (in: J Rheumatol 39, 7, 1473, 2012). The option "compliance with the zero point of start of oscillatory motion" is activated. At each measurement point, the value of the torque is recorded, and then the coefficient of friction (COF) is calculated according to the formula: COF=torque/(⅓×diameter of the disc×normal force). For each formulation, the measurement is replicated 5 times. The value of the coefficient of friction is reported by extrapolation of the intercept at the start of each COF curve as a function of time ($COF_0$, Table 7).

TABLE 9

Lubricating capacity of formulations of fungal origin carboxymethyl chitosan

| No (concentration) | Coefficient of friction ($COF_0$) | | |
|---|---|---|---|
| | Measurement 1 | Measurement 2 | Measurement 3 |
| Synovial fluid from an arthritis patient | 20 | 40 | 12 |
| CC-8 (2%) | 1.2 | 1.7 | 1.3 |
| CC-8 (1%) | 2.4 | 3.7 | 3.9 |
| CC-19 (2%) | 4.0 | 3.2 | 3.0 |
| CC-3 (2%) | 6.2 | 6.1 | 6.0 |
| Synvisc ® | 3.2 | 3.1 | 3.8 |
| HA-2 | 6.7 | 6.3 | 6.6 |
| HA-3 | 5.3 | 5.6 | 4.5 |
| HA-4 | 6.8 | 6.7 | 6.0 |
| HA-5 | 29.4 | 13.3 | 26.1 |

In the presence of the formulations of 2% and 1% carboxymethyl chitosan, the coefficient of friction is low, of the same order of magnitude or even lower than commercially available products for intra-articular and ophthalmic use, and significantly weaker than that of an arthritic synovial fluid, under the conditions of measurement. It is inferred therefrom that the carboxymethyl chitosan formulations have the potential to act as a lubricant by reducing the friction between two surfaces, for example the cartilage surfaces of a joint after intra-articular injection or the ocular surface after instillation in the form of drops. The formulations of fungal origin CCs are more effective in reducing friction than the formulation of animal origin CC-3.

Example 10—Use of Fine Needles for the Administration of a Formulation of Fungal Origin Carboxymethyl Chitosan Via Intradermal Route This example seeks to show that a formulation of 2% of fungal origin carboxymethyl chitosan can be easily injected into the dermis, in particular by making use of very fine needles designed for injection into the surface layers of the dermis. The test consists in measuring the force necessary to eject the product out of the syringe equipped with a needle, at a given rate of ejection, by means of a compression test bench. It is empirically considered that the injection of the product is easy and comfortable for the doctor and the patient when the ejection force as measured by this test is less than 50 Newton, and the ejection takes place in a regular and smooth manner. It is advantageous to be able to administer the product by using needles having a diameter of less than 0.3 mm (30 G) in order to minimise the pain and bleeding on injection as well as the subsequent risk of hematomas and skin redness.

A reference fungal origin carboxymethyl chitosan CC-20 is produced according to the general method of CC-8 indicated in Example 3, starting from an "ultra-high" type chitosan, with the following modifications: for 10 g of chitosan, use is made of 228 ml of isopropanol, 57 ml of 40% sodium hydroxide, and 47 g of MCA. The reaction is carried out at 35° C. for a period of 23 hours. For 15 g of intermediate carboxymethyl chitosan, use is made of 7.5 ml of acetic anhydride with each addition, and 3 additional purification cycles are applied prior to drying and recovery of the final carboxymethyl chitosan. The characteristics of CC-20 are as follows: DA 53% and DS 85% (determined by carbon 13 NMR), soluble in water at any pH (according to the method described here above), forming a transparent and non-opalescent solution, with zeta potential at pH 7.5 estimated at −24 mV (from the polynomial regression of the zeta potential curve as a function of the DS).

A 2% (m/m) CC-20 formulation is prepared as described in Example 3. The formulation is packaged in a 1 ml glass syringe (BD-Medical) on which the needle is adapted. By means of a MultiTest 2.5-i compression test bench (Mecmesin) equipped with a 100N compression cell, the force required for ejecting the product is measured by applying a constant ejection rate of 80 mm/min. The maximum force tolerated by the equipment is approximately 70 Newton. The following needles are tested: 30 G, 32 G, 33 G and Invisible Needle™ (TSK Laboratory), the dimensions of which (exterior diameter×length) are reported in Table 10.

For comparison purposes, commercially available products based on non-crosslinked hyaluronic acid (references HA-6, HA-7) and crosslinked hyaluronic acid (HA-8), indicated for skin rejuvenation via the intradermal route, are evaluated according to the same method, in their original syringe. The results are reported in Table 10.

Example 11—Low Concentration Formulations of Fungal Origin Carboxymethyl Chitosan with a View to an Indication as Ophthalmic Drops This example seeks to show that a low concentration solution of fungal origin carboxymethyl chitosan may be applied for the preparation of ophthalmic drops intended for use for reducing the symptoms of disorders of the ocular surface or for protecting the same. In addition to physiological characteristics, that is to say preferentially a pH of around 7.2 and an osmolality of around 200 mOsm/kg, the ophthalmic drops should preferably have the following physicochemical properties: low refractive index (close to 1.33) and capacity to minimise friction between the ocular surface and the conjunctiva and the eyelids (lubricating capacity). Finally, its rheological profile is such that the product is not too fluid to be able to be deposited on the eye, but rather it spreads out in a homogeneous manner and it is not sticky. Its rheological profile should also be such that the fluttering or blinking of the eyelids is easy, without accumulation, that is to say a low viscosity at a high shear rate. In particular, Orobia et al. consider that the viscosity during ocular movement (excluding fluttering of the eyelids) is advantageously greater than 10 mPa·s, for example around 20 mPa·s (in: Clinical Ophthalmology 12, 453, 2018). It should be noted here that the value of the viscosity is liable to vary according to the measurement method, and in particular the equipment, the mode of measurement and the parameters, the temperature and the shear rate applied to the product tested.

A reference fungal origin carboxymethyl chitosan CC-21 is produced according to the same method as the CC-20 indicated in Example 10. A comparison is done of the molecular structures of CC-20 and CC-21 in acid form, by means of Fourrier transform infrared spectrometry making use of a Nicolet iS5 spectrometer equipped with an ID7-ATR (Thermo Scientifics), according to the method described by Chen et al. (Carbohydrate Polymers 53, 355, 2003). It is determined that their molecular structures are 99% identical in the wavelength region of 1200 to 1800 $cm^{-1}$, and as a consequence that their DA and DS are similar.

Two formulations of carboxymethyl chitosan CC-21, of concentration 0.7% and 0.4% (m/m), in a phosphate buffer with glycerol are prepared. The pH is adjusted to 7.2 t 0.2 and the osmolality to 200±20 mOsm/kg, and then the formulations are filtered, following which their lubricating capacity and their viscosity profile are characterised according to the methods described here below. The hyaluronic acid (HA) based ophthalmic drops of variable composition, are characterised according to the same methods (HA-5 to HA-9). The results are reported in Table 11 b.

Method for Measurement of the Coefficient of Friction (Suitable for Ophthalmic Drops)

The capacity to lubricate, that is to say to reduce the friction between two surfaces that are in contact, is evaluated by measuring the coefficient of friction between two discs made of polyacrylate biomaterial that is identical to those indicated in Example 9. The two discs are fixed to the upper and lower geometries of a DHR-2 rheometer (TA Instruments), a volume of approximately 100 µL of the product to be tested is placed on the lower disc, then the upper geometry is lowered until contact is brought about between the two discs, up to an imposed normal force of 5 Newton. The measurement of coefficient of friction is carried out at 25° C. for a period of 60 seconds, at constant normal force (5 N), oscillation frequency of 6 rad/s and angle of deformation of approximately 1.71 radian, according to a protocol adapted from Waller et al. (J Rheumatol 39, 7, 1473, 2012) and the parameters mimicking the kinematic conditions of blinking of the eyelids described by Kwon et al. (J Royal Society Interface 10, 2, 2013). The option "compliance with the zero point of start of oscillatory motion" is activated. At each measurement point, the value of the torque is recorded, then the coefficient of friction (COF) is calculated according to the formula: COF=torque (⅓×diameter of the disc× normal force). The mean COF value is determined between 0 and 60 s. The mean coefficient of friction as well as the standard deviation of 5 consecutive measurements are thus calculated. The minimum value of the COF is 52 in the case where two surfaces are not in contact. The upper limit of COF corresponds to the case where the two discs are no longer in motion in relation to each other.

Given that the COF value is variable from one series to another, it is necessary to characterise the products to be compared in the same given series, making use of the same discs and in a random order. A scale of relative scores is then used in order to classify the products tested in the same series, from the most effective (score 1) to the least effective (score 3), according to the criteria in Table 11a. The limits "$COF_A$" and "$COF_B$" are defined by the COF of two commercially available ophthalmic drops taken as reference for each series: drops A (composed of 0.15% HA and 0.25% carbomer) and drops B (0.15% HA). According to this scale, it is advantageous for the score for reduction of friction to be 1 or 2, and preferably 1, for use as a lubricating drop for lubricating the ocular surface. For products with a score of 3, the lubricating capacity is not satisfactory and the variation over the measurement is significant.

TABLE 11a

Scale of Lubrication Scores (Reduction of Friction)

| Score | COF Limits |
|---|---|
| 1 | ≤1.1 × $COF_A$ |
| 2 | >1.1 × $COF_A$ and ≤1.1 × $COF_B$ |
| 3 | >1.1 × $COF_B$ |

Methods for Measurement of Viscosity as a Function of Shear

Simmons et al. have determined that the shear rate during open eye movements is around 10 $s^{-1}$ and the shear rate during eyelid fluttering is around 10000 $s^{-1}$ (in: Clinical Ophthalmology 11, 1637, 2017). The rheometric measurement method is selected according to the range of shear rates to be studied and taking into account that the products are low viscosity fluid solutions:

Shear range corresponding to ocular movement. The viscosity is measured in rotational mode with a flow sweep test by means of a stress-controlled DHR-2 rheometer (TA Instruments) equipped with a Peltier plate and a "cone" type geometry of 60 mm diameter and a truncation angle of 2°. The product is equilibrated for 1 minute to 37° C., the temperature being controlled by the Peltier. In order to avoid evaporation, the system is equipped with a solvent trap and a metal cover. Then, the flow sweep test is started and the viscosity is measured as a function of the shear rate, from 0.001 $s^{-1}$ to 100 $s^{-1}$. The viscosity value at 10 $s^{-1}$ is reported.

Shear range corresponding to the fluttering of the eyelids. The viscosity is measured in rotational mode with a flow sweep test by means of a stress-controlled DHR-2 rheometer (TA Instruments) equipped with a "Double gap couette (cylindrical)" type geometry and a Peltier concentric cylinder, and equipped with a solvent trap and a metal cover. The product is equilibrated for 1 minute to 37° C., and then a variable shear rate is applied varying from 0.001 $s^{-1}$ to 10000 $s^{-1}$. The viscosity value at 10000 $s^{-1}$ is thus then compared with the value at 10 $s^{-1}$.

TABLE 11b

Characteristics of low concentration formulations of fungal origin carboxymethyl chitosan and of hyaluronic acid-based ophthalmic drops

| Reference | Refractive index | Viscosity at 10 $s^{-1}$ (mPa · s) | Viscosity at 10000 $s^{-1}$ (mPa · s) | Friction Reduction Score |
|---|---|---|---|---|
| Phosphate buffer with glycerol | 1.3348 | N/A | N/A | Not measurable |
| CC-21 0.7% | 1.3358 | 27 | Lower than viscosity at 10 $s^{-1}$ | 1 |
| CC-21 0.4% | 1.3353 | 10 | | 1 |
| HA-5 | 1.3343 | 6 | Lower than viscosity at 10 $s^{-1}$ | 2 |
| HA-10 | 1.3386 | 3 | | 2 |
| HA-11 | 1.3350 | 6 | | 2 |
| HA-12 | 1.3346 | 50 | | 2 |

The results confirm that the two formulations of fungal carboxymethyl chitosan CC-21 meet the technical specifications for ophthalmic drops: they have a low refractive index, a satisfactory coefficient of friction (score 1, that is to say as effective as the most lubricating commercially available drops), a viscosity of 10 to 30 mPa·s in conditions of ocular movement and a lower viscosity in conditions of fluttering of eyelids. Without the carboxymethyl chitosan, the phosphate buffer supplemented with glycerol does not provide the means to meet the technical specifications for ophthalmic drops. Finally, it is noted that the viscosity may be reduced by reducing the concentration of carboxymethyl chitosan (for example from 0.7 to 0.4%) without adversely altering the ability to reduce friction (score 1).

The invention claimed is:

1. A method of therapeutic treatment for osteoarthritis or repairing a cartilage defect, said method comprising administering a carboxyalkyl chitosan to a subject in need thereof, wherein said carboxyalkyl chitosan is administered via injection into the synovial fluid or via implantation in the cartilage, wherein said carboxyalkyl chitosan comprises glucosamine units, N-acetyl-glucosamine units, and glucosamine units substituted by a carboxyalkyl group, wherein the carboxyalkyl chitosan is N,O-carboxyalkyl chitosan and has:
   a zeta potential, measured at pH 7.5, that is lower than or equal to −18 mV;
   a degree of acetylation in a range of about 40% to about 80%, expressed at the number of moles of N-acetyl-glucosamine units relative to the number of moles of total units; and
   a degree of substitution by the carboxyalkyl group that is greater than 70% expressed as the number of moles of the substituent carboxyalkyl group relative to the number of moles of total units, and
wherein the carboxyalkyl chitosan is water-soluble at a pH less than 3.5 and at a physiological pH and is sufficiently pure and suitable for providing a non-opalescent aqueous solution for injection, implantation, or instillation to a human or animal subject.

2. The method of claim 1, wherein said carboxyl chitosan has having a zeta potential, measured at pH 7.5, that is less than or equal to −20 mV.

3. The method of claim 1, wherein the degree of substitution by the carboxyalkyl group is greater than 70% and no greater than 200% expressed as the number of moles of the substituent carboxyalkyl group relative to the number of moles of total units.

4. The method of claim 1, wherein the chitosan is derived from the group consisting of Basidiomycetes, mycelium of Ascomycetes, and a mixture thereof.

5. The method of claim 1, wherein the carboxyalkyl chitosan is suitable for providing a transparent aqueous solution.

6. The method of claim 1, wherein the carboxyalkyl chitosan is sterilized.

7. The method of claim 1, wherein said carboxyalkyl chitosan is comprised in an injectable composition.

8. The method of claim 1, wherein said carboxyalkyl chitosan is comprised in an aqueous solution.

9. The method of claim 8, wherein said aqueous solution further comprises hyaluronic acid or sodium hyaluronate, either crosslinked or not crosslinked by covalent bonds.

10. The method of claim 8, wherein said aqueous solution further comprises a reducing sugar.

11. The method of claim 8, wherein said aqueous solution is comprised in a medical device.

12. The method of claim 1, wherein said carboxyalkyl chitosan is comprised in a pharmaceutical composition.

13. The method of claim 12, wherein said pharmaceutical composition further comprises hyaluronic acid or sodium hyaluronate, either crosslinked or not crosslinked by covalent bonds.

14. The method of claim 12, wherein said pharmaceutical composition is selected from the group consisting of: an injectable pharmaceutical composition suitable for delivery via an injectable medical device, an implantable pharmaceutical composition suitable for delivery via an implantable medical device, and a pharmaceutical composition suitable for instillation via a instillation medical device.

15. The method of claim 1, wherein the carboxyalkyl chitosan is instilled or injected via an intra-articular route.

16. The method of claim 1, wherein said carboxyalkyl chitosan is water-soluble at a pH in a range of 3.1 to 9.

17. The method of claim 7, wherein the carboxyalkyl chitosan is water-soluble at least in the pH range of 3.1 to 9.

18. The method of claim 8, wherein said carboxyalkyl chitosan is soluble at a pH in a range of 3.1 to 9.

19. The method of claim 18, wherein said aqueous solution further comprises hyaluronic acid or sodium hyaluronate, either crosslinked or not crosslinked by covalent bonds.

20. The method of claim 11, wherein said carboxyalkyl chitosan is soluble at a pH in a range of 3.1 to 9.

21. The method of claim 12, wherein said carboxyalkyl chitosan is soluble at a pH in a range of 3.1 to 9.

22. The method of claim 2, wherein said carboxyalkyl chitosan is soluble at a pH in a range of 3.1 to 9.

23. The method of claim 22, wherein said carboxyalkyl chitosan is administered via injection into the synovial fluid after mixing with blood.

24. The method of claim 22, wherein said carboxyalkyl chitosan is administered via implantation into the cartilage.

* * * * *